US011957571B2

(12) United States Patent
Aharoni

(10) Patent No.: US 11,957,571 B2
(45) Date of Patent: *Apr. 16, 2024

(54) APPARATUS FOR USE IN IMPLANTING INTRAOCULAR LENSES AND METHOD OF PREPARING APPARATUS FOR USE

(71) Applicant: Samsara Vision, Inc., Far Hill, NJ (US)

(72) Inventor: Eli Aharoni, Tel Aviv (IL)

(73) Assignee: Samsara Vision, Inc., Far Hill, NJ (US)

( * ) Notice: Subject to any disclaimer, the term of this patent is extended or adjusted under 35 U.S.C. 154(b) by 406 days.

This patent is subject to a terminal disclaimer.

(21) Appl. No.: 17/177,731

(22) Filed: Feb. 17, 2021

(65) Prior Publication Data

US 2021/0236271 A1 Aug. 5, 2021

Related U.S. Application Data

(63) Continuation of application No. 15/963,309, filed on Apr. 26, 2018, now Pat. No. 10,925,722.

(51) Int. Cl.
*A61F 2/16* (2006.01)

(52) U.S. Cl.
CPC ........... *A61F 2/1664* (2013.01); *A61F 2/167* (2013.01); *A61F 2002/16902* (2015.04)

(58) Field of Classification Search
CPC .................... A61F 2/1664; A61F 2/167; A61F 2002/16902
See application file for complete search history.

(56) References Cited

U.S. PATENT DOCUMENTS

| 5,006,123 A | 4/1991 | Soll et al. |
| 5,354,335 A | 10/1994 | Lipshitz et al. |
| 5,391,202 A | 2/1995 | Lipshitz et al. |
| 5,814,103 A | 9/1998 | Lipshitz et al. |

(Continued)

FOREIGN PATENT DOCUMENTS

| EP | 3560457 | 10/2019 |
| GB | 2242835 | 10/1991 |

(Continued)

OTHER PUBLICATIONS

European Search Report dated Jul. 26, 2019 which issued during the prosecution of Applicant's European App No. 191698646.

(Continued)

*Primary Examiner* — Phong Son H Dang
(74) *Attorney, Agent, or Firm* — Locke Lord LLP; Gabrielle L. Gelozin

(57) ABSTRACT

Apparatus for use in implanting intraocular lenses, the apparatus including an axial elongate hollow conduit having first and second ends and defining an intraocular lens injection pathway extending along a longitudinal axis, the axial elongate hollow conduit being formed at the first end with a syringe connector defining a removable syringe mounting location and a pusher element located within the axial elongate hollow conduit between the syringe connector and the second end, at least one of the axial elongate hollow conduit and the pusher element being formed with mutually communicating conduits for enabling viscoelastic material to pass through the syringe connector and the pusher element to a location between the pusher element and the second end of the axial elongate hollow conduit.

8 Claims, 22 Drawing Sheets

(56) References Cited

U.S. PATENT DOCUMENTS

| | | |
|---|---|---|
| 5,876,442 A | 3/1999 | Lipshitz et al. |
| 5,928,283 A | 7/1999 | Gross et al. |
| 6,007,579 A | 12/1999 | Lipshitz et al. |
| 6,066,171 A | 5/2000 | Lipshitz et al. |
| 6,569,199 B1 | 5/2003 | Dotan et al. |
| 6,596,026 B1 | 7/2003 | Gross et al. |
| 6,972,032 B2 | 12/2005 | Aharoni et al. |
| 7,001,427 B2 | 2/2006 | Aharoni et al. |
| 7,101,397 B2 | 9/2006 | Aharoni |
| 7,727,277 B2 | 6/2010 | Aharoni et al. |
| 7,736,390 B2 | 6/2010 | Aharoni et al. |
| 7,776,087 B2 | 8/2010 | Aharoni et al. |
| 7,842,086 B2 | 11/2010 | Dotan et al. |
| 7,918,886 B2 | 4/2011 | Aharoni et al. |
| 8,088,161 B2 | 1/2012 | Aharoni et al. |
| 8,133,273 B2 | 3/2012 | Aharoni et al. |
| 8,398,651 B2 | 3/2013 | Martin et al. |
| 9,358,102 B2 | 6/2016 | Aharoni et al. |
| 10,010,409 B2 | 7/2018 | Attinger |
| 10,426,602 B2 | 10/2019 | Tseng et al. |
| 10,470,875 B2 | 11/2019 | Fayyaz et al. |
| 10,925,722 B2 | 2/2021 | Aharoni |
| 2003/0187455 A1 | 10/2003 | Kobayashi et al. |
| 2004/0117012 A1 | 6/2004 | Vincent |
| 2005/0065602 A1 | 3/2005 | Aharoni et al. |
| 2005/0154457 A1 | 7/2005 | Aharoni et al. |
| 2006/0004446 A1 | 1/2006 | Aharoni et al. |
| 2006/0142781 A1 | 6/2006 | Pynson et al. |
| 2006/0235428 A1 | 10/2006 | Silvestrini |
| 2007/0027541 A1 | 2/2007 | Aharoni et al. |
| 2008/0097459 A1 | 4/2008 | Kammerlander et al. |
| 2008/0200921 A1 | 8/2008 | Downer |
| 2009/0024136 A1 | 1/2009 | Martin et al. |
| 2009/0216244 A1 | 8/2009 | Pynson |
| 2009/0240257 A1 | 9/2009 | Meyer |
| 2010/0145445 A1 | 6/2010 | Aharoni et al. |
| 2010/0256651 A1 | 10/2010 | Jani et al. |
| 2010/0331808 A1 | 12/2010 | Py et al. |
| 2011/0054599 A1 | 3/2011 | Dotan et al. |
| 2011/0082463 A1 | 4/2011 | Inoue |
| 2012/0095554 A1 | 4/2012 | Aharoni et al. |
| 2012/0245591 A1 | 9/2012 | Matthews |
| 2013/0226193 A1 | 8/2013 | Kudo et al. |
| 2014/0012277 A1 | 1/2014 | Matthews et al. |
| 2014/0257317 A1 | 9/2014 | Safabash |
| 2014/0276901 A1 | 9/2014 | Auld |
| 2014/0371851 A1 | 12/2014 | Aharoni |
| 2014/0371852 A1 | 12/2014 | Aharoni et al. |
| 2015/0342726 A1 | 12/2015 | Deacon et al. |
| 2016/0022488 A1 | 1/2016 | Dimmig et al. |
| 2016/0262877 A1 | 9/2016 | Aharoni |
| 2016/0278913 A1 | 9/2016 | Aharoni et al. |
| 2017/0172727 A1 | 6/2017 | Kanner et al. |
| 2019/0083237 A1 | 3/2019 | Valle et al. |
| 2019/0328510 A1 | 10/2019 | Aharoni |

FOREIGN PATENT DOCUMENTS

| | | |
|---|---|---|
| JP | 2007-007332 | 1/2007 |
| WO | 2011/021225 | 2/2011 |

OTHER PUBLICATIONS

Notice of Allowance dated Sep. 12, 2018, which issued during the prosecution of U.S. Appl. No. 15/030,803.

An English translation of an Office Action dated Jul. 24, 2018 which issued during the prosecution of Japanese Patent Application No. 2016-551109.

Notice of Allowance dated Oct. 30, 2020, which issued during the prosecution of U.S. Appl. No. 15/963,309.

An Office Action dated Dec. 27, 2019, which issued during the prosecution of U.S. Appl. No. 15/963,309.

Notice of Allowance dated May 27, 2020, which issued during the prosecution of U.S. Appl. No. 15/963,309.

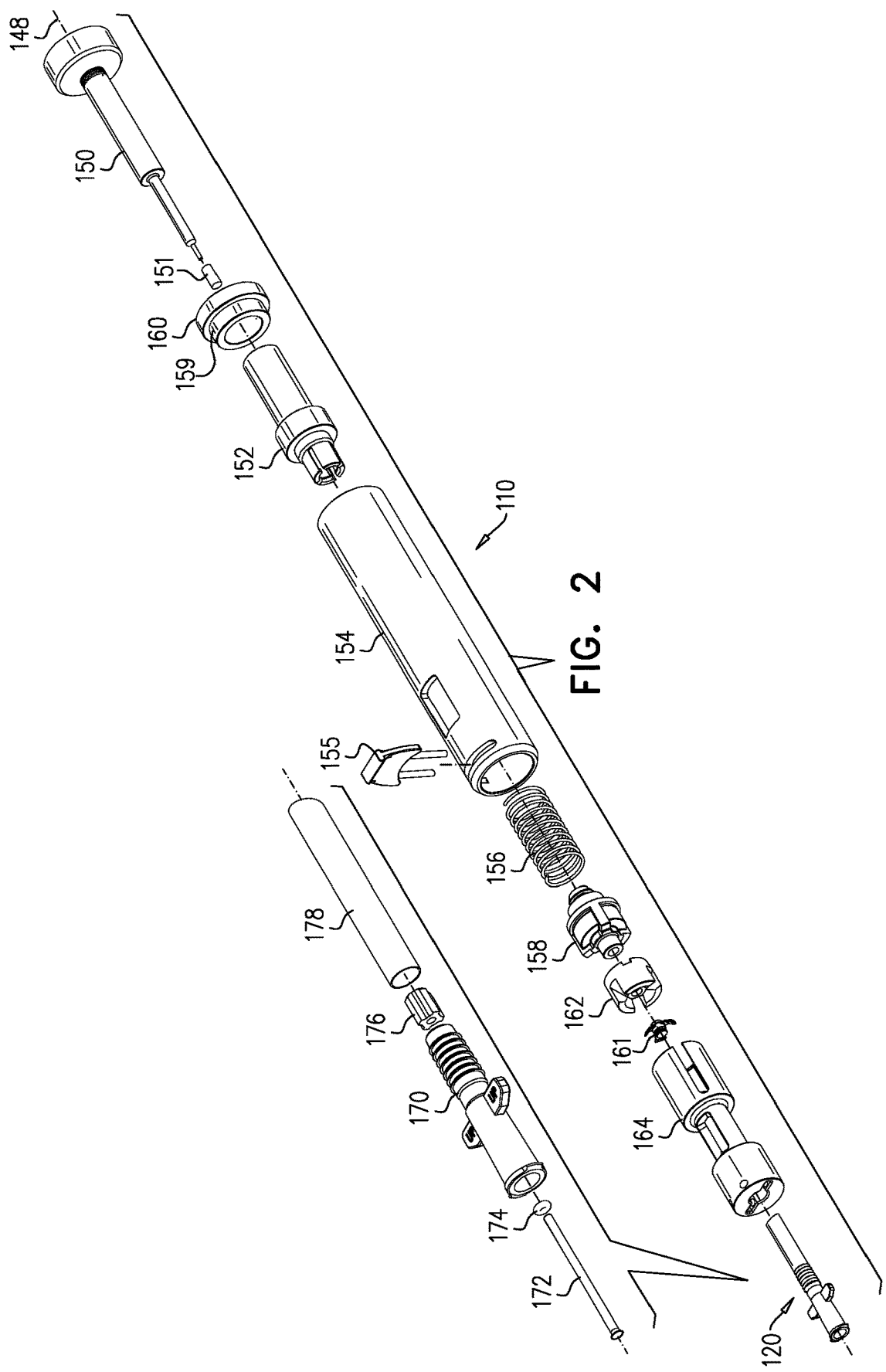

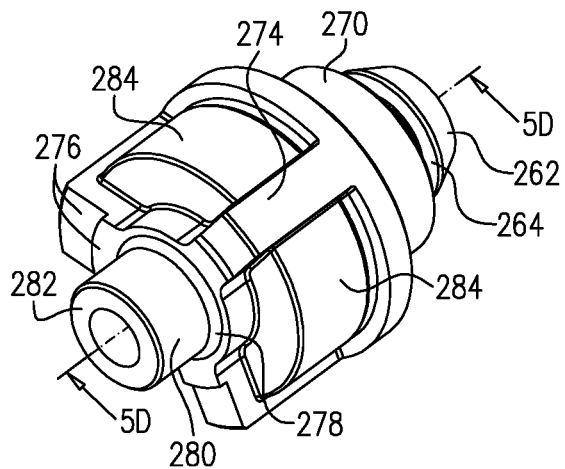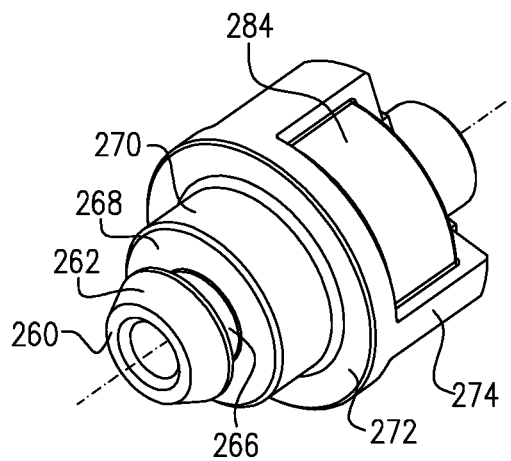
FIG. 5A  FIG. 5B
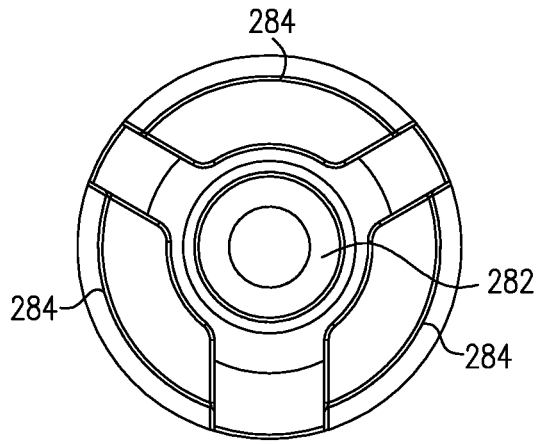
FIG. 5C
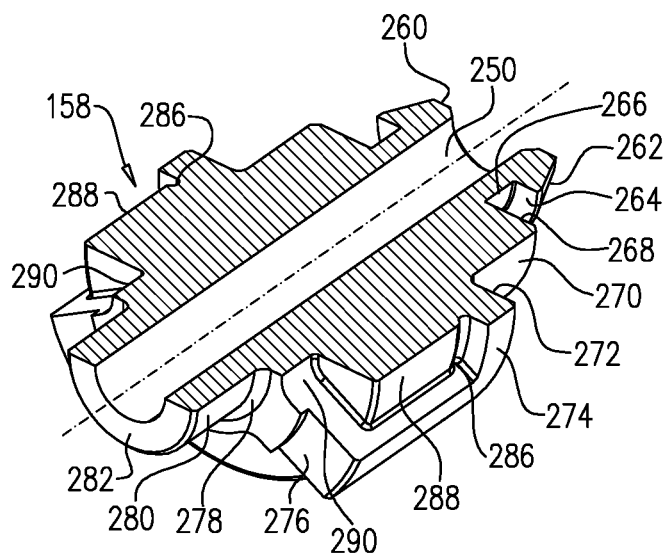
FIG. 5D

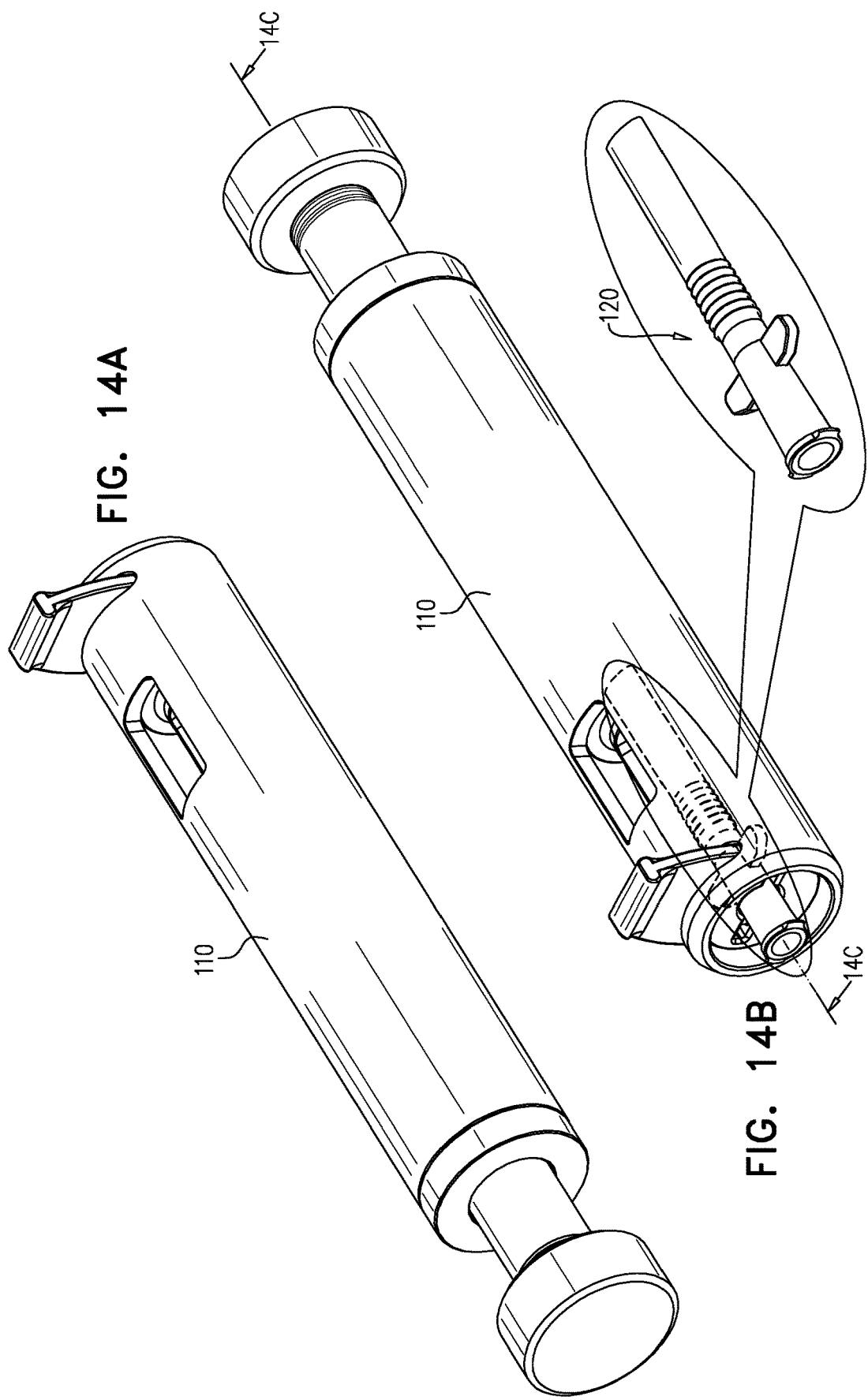

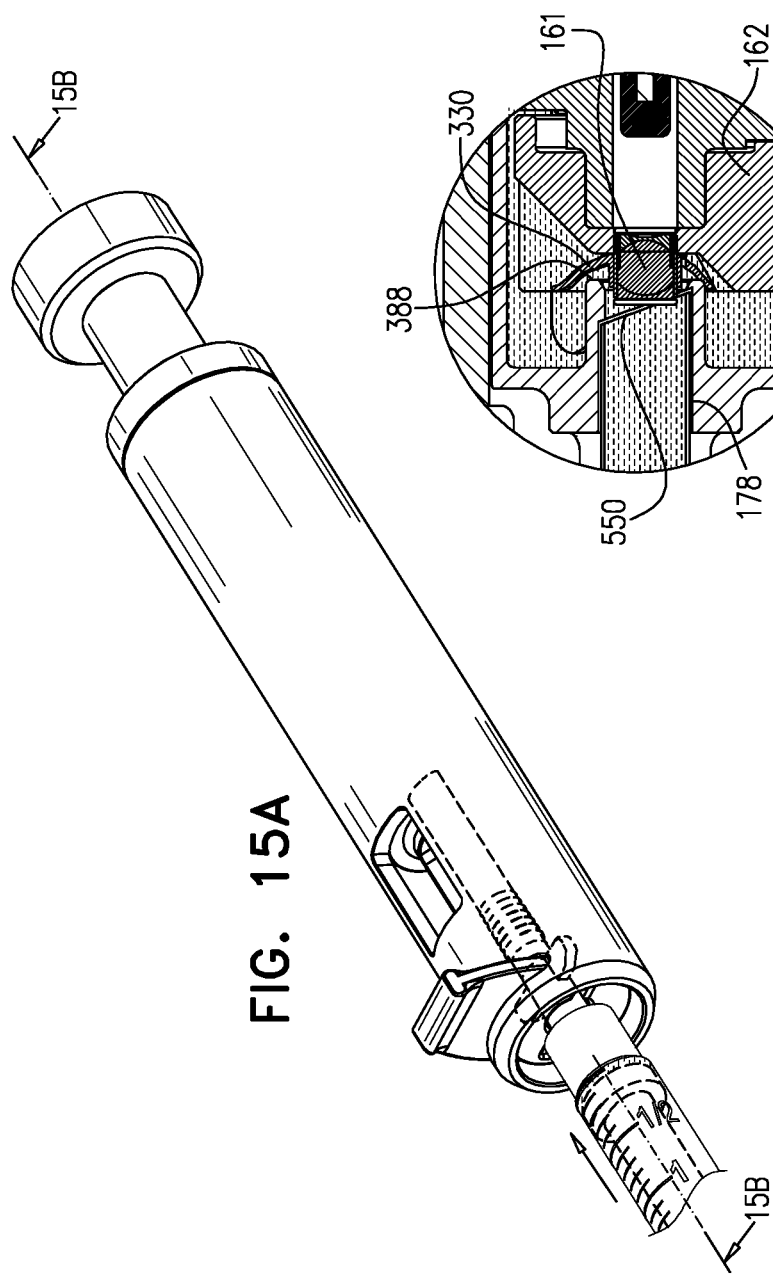

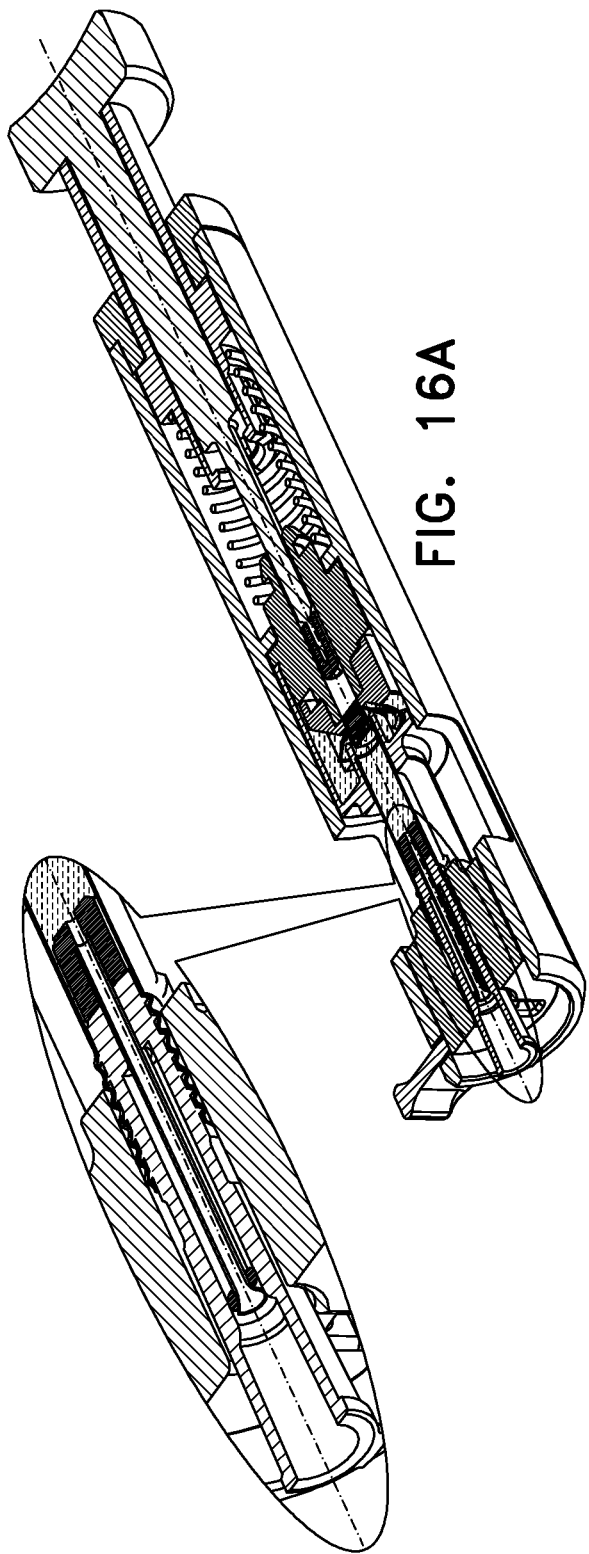
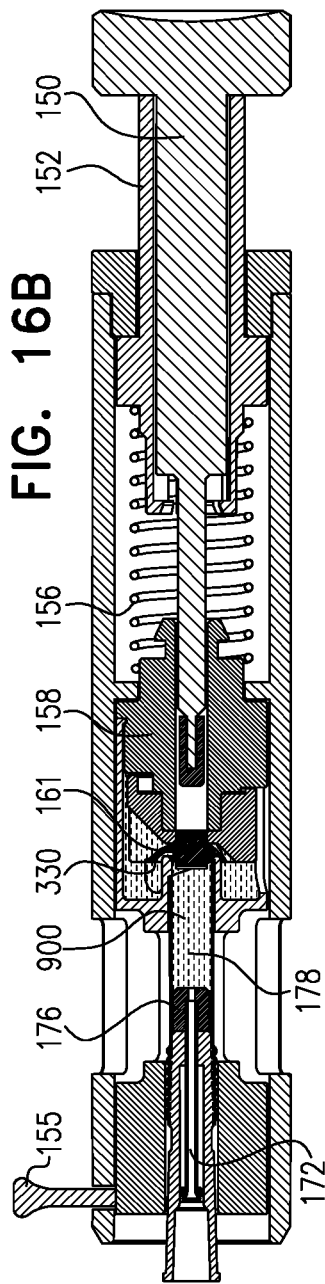
FIG. 16A
FIG. 16B

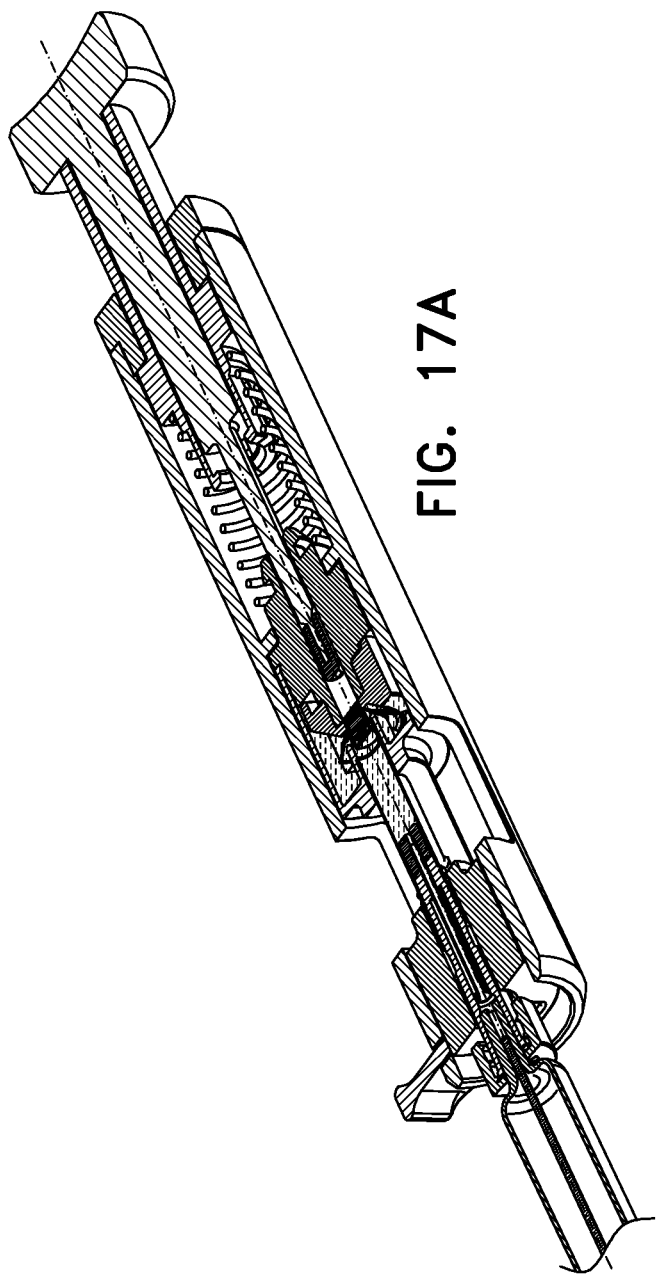
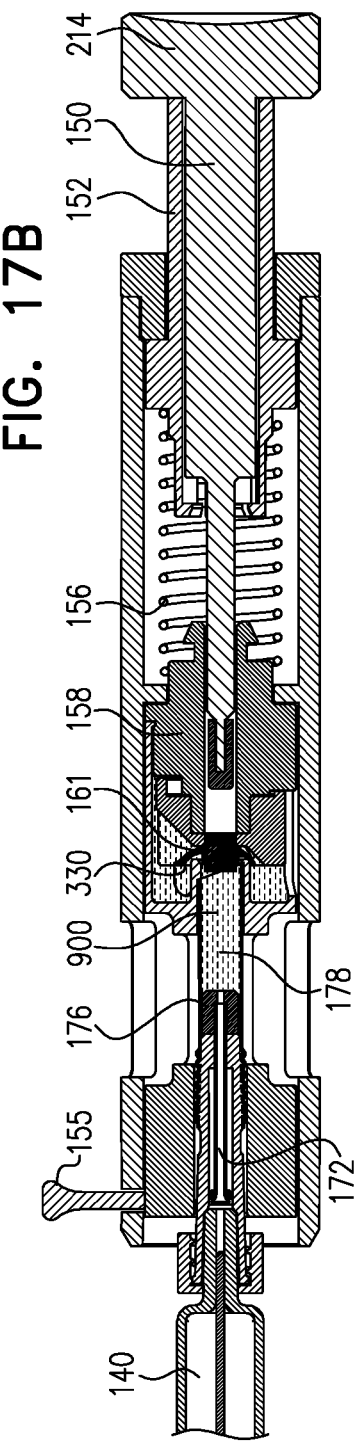
FIG. 17A
FIG. 17B

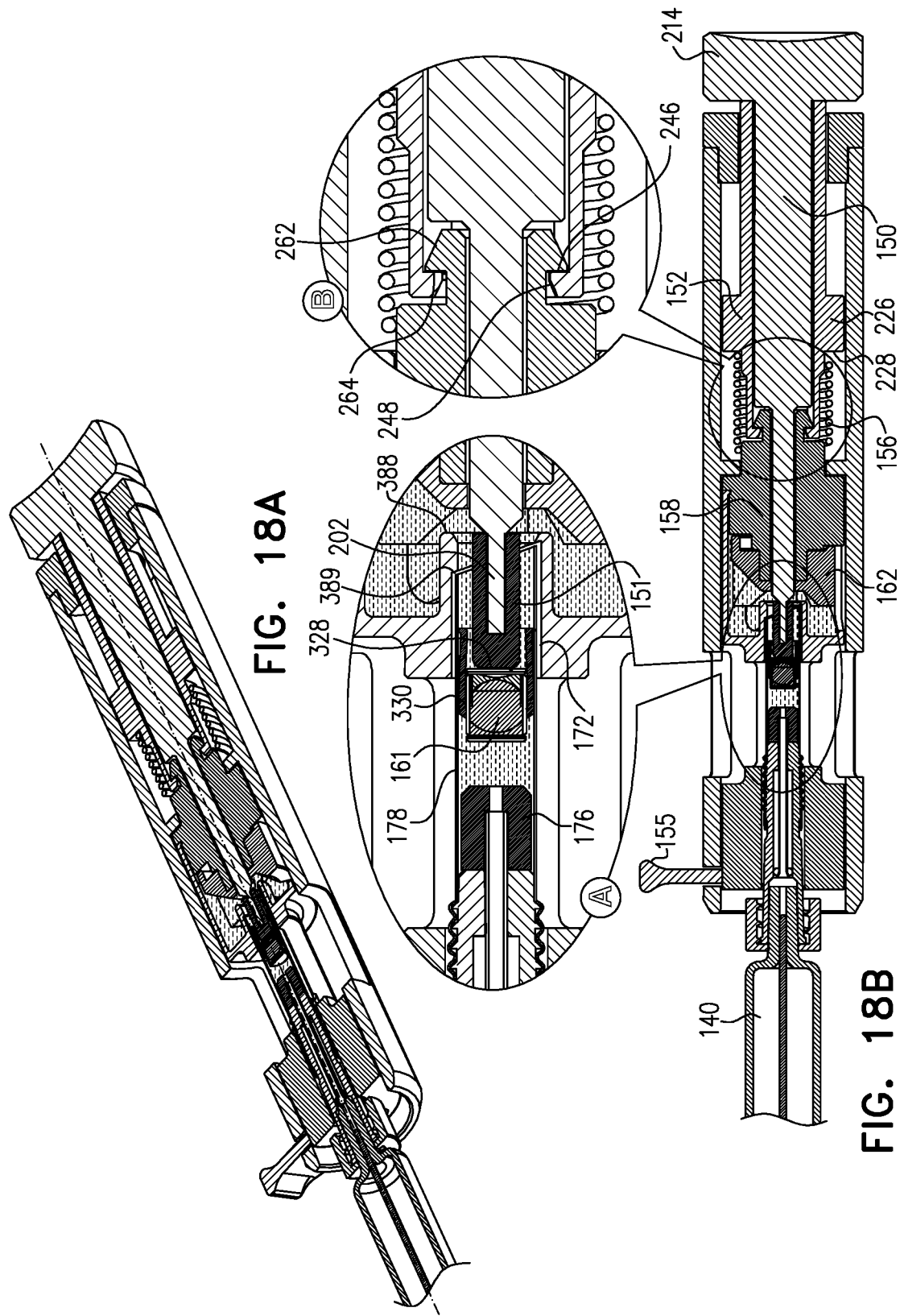

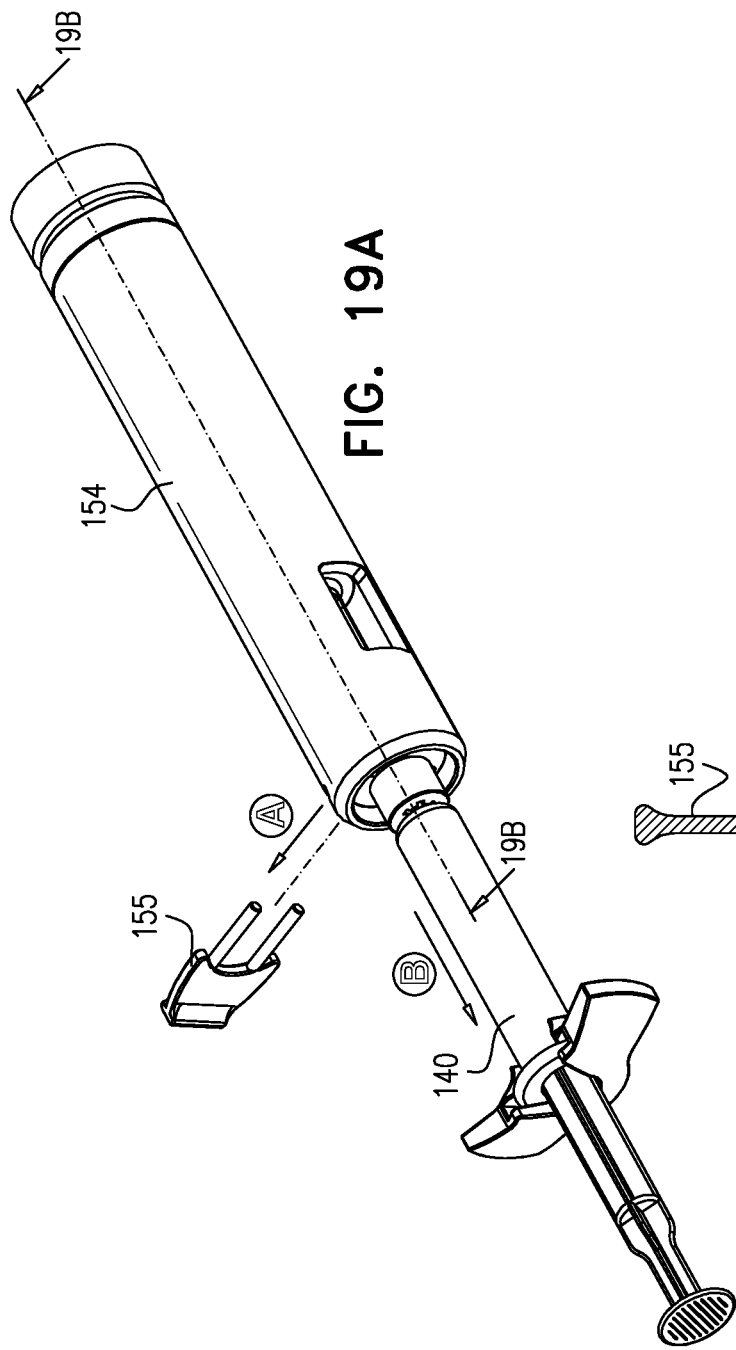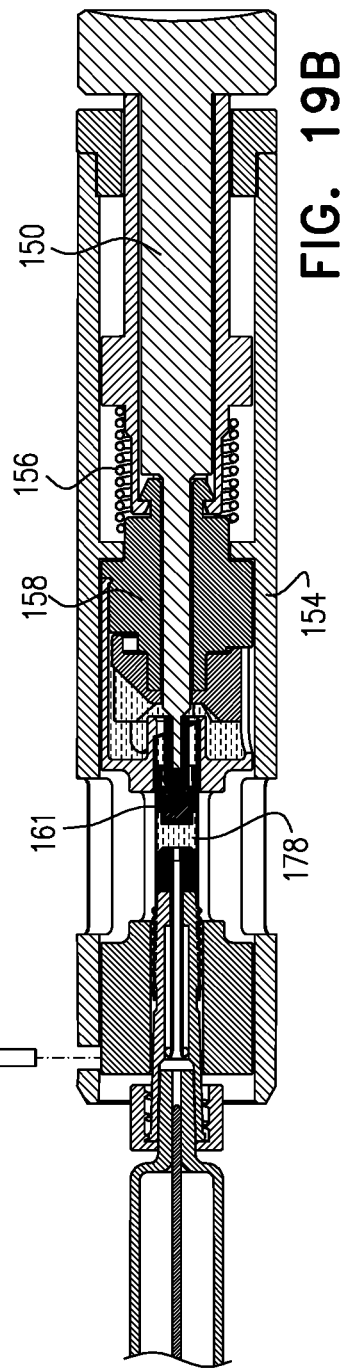

APPARATUS FOR USE IN IMPLANTING INTRAOCULAR LENSES AND METHOD OF PREPARING APPARATUS FOR USE

REFERENCE TO RELATED APPLICATIONS

The present application is a continuation application of U.S. patent application Ser. No. 15/963,309, filed Apr. 26, 2018, entitled APPARATUS FOR USE IN IMPLANTING INTRAOCULAR LENSES AND METHOD OF PREPARING APPARATUS FOR USE, now U.S. Pat. No. 10,925,722, the contents of which is incorporated herein by reference in its entirety.

U.S. Pat. Nos. 5,354,335; 5,391,202; 5,814,103; 5,876,442; 5,928,283; 6,007,579; 6,066,171; 6,569,199; 6,596,026; 6,972,032; 7,001,427; 7,101,397; 7,736,390; 7,727,277; 7,776,087; 7,842,086; 7,918,886; 8,088,161; 8,133,273 and 9,358,102; and U.S. Patent Publication Nos. 2005/0065602; 2005/0154457; 2006/0004446; 2007/0027541; 2010/0145445; 2011/0054599; 2012/0095554; 2014/0371851; 2014/0371852; 2016/0262877 and 2016/0278913.

FIELD OF THE INVENTION

The present invention relates to medical devices generally and more particularly to devices for use in implanting intraocular lenses.

BACKGROUND OF THE INVENTION

Various types of intraocular lenses are known, examples of which are described in the above-referenced patents and patent applications. Various tools for use in implanting intraocular lenses are also known.

SUMMARY OF THE INVENTION

The present invention seeks to provide improved apparatus for use in implanting intraocular lenses.

There is thus provided in accordance with a preferred embodiment of the present invention apparatus for use in implanting intraocular lenses, the apparatus including an axial elongate hollow conduit having first and second ends and defining an intraocular lens injection pathway extending along a longitudinal axis, the axial elongate hollow conduit being formed at the first end with a syringe connector defining a removable syringe mounting location and a pusher element located within the axial elongate hollow conduit between the syringe connector and the second end, at least one of the axial elongate hollow conduit and the pusher element being formed with mutually communicating conduits for enabling viscoelastic material to pass through the syringe connector and the pusher element to a location between the pusher element and the second end of the axial elongate hollow conduit.

In accordance with a preferred embodiment of the present invention the apparatus for use in implanting intraocular lenses also includes a dual purpose elongate hollow tube, fixed to the pusher element, the dual purpose elongate hollow tube having a fluid entry end adjacent the syringe connector and a fluid outlet end, the dual purpose elongate hollow tube defining a hollow pusher rod and being displaceable along the longitudinal axis within and relative to the axial elongate hollow conduit towards the second end, thereby displacing the pusher element along the axis towards the second end. Additionally or alternatively, the axial elongate hollow conduit includes a first relatively rigid housing portion, which defines the syringe connector, and a relatively flexible sleeve portion, which is mounted onto the relatively rigid housing portion. Additionally, the flexible sleeve portion is formed with an angled edge defining the second end of the axial elongate hollow conduit.

In accordance with a preferred embodiment of the present invention the hollow pusher rod is slidably and sealingly disposed within the axial elongate hollow conduit. Additionally, the hollow pusher rod is slidably and sealingly disposed within the axial elongate hollow conduit by engagement with an O-ring.

Preferably, the hollow pusher rod is formed with a tapered opening, which communicates with a throughgoing cylindrical bore extending axially therethrough. Additionally, the throughgoing cylindrical bore communicates with a conduit extending through the pusher element, thereby to define part of the mutually communicating conduits for enabling viscoelastic material to pass through the syringe connector and the pusher element to a location between the pusher element and the second end of the axial elongate hollow conduit.

There is also provided in accordance with another preferred embodiment of the present invention a method of preparing an intraocular lens for injection, the method including providing apparatus for use in implanting intraocular lenses, the apparatus including an axial elongate hollow conduit having first and second ends and defining an intraocular lens injection pathway extending along a longitudinal axis, a syringe connector defining a removable syringe mounting location, the syringe connector being located at a first end of the axial elongate hollow conduit and a pusher element located within the axial elongate hollow conduit between the syringe connector and the second end, at least one of the axial elongate hollow conduit and the pusher element being formed with mutually communicating conduits for enabling viscoelastic material to pass through the syringe connector and the pusher element to a location between the pusher element and the second end of the axial elongate hollow conduit, injecting a viscoelastic material via the mutually communicating conduits to the location between the pusher element and the second end of the axial elongate hollow conduit and thereafter inserting, via the second end of the axial elongate hollow conduit, an intraocular lens into the viscoelastic material at the location between the pusher element and the second end of the axial elongate hollow conduit.

In accordance with a preferred embodiment of the present invention the injecting takes place via the syringe connector at the first end.

Preferably, the axial elongate hollow conduit is mounted onto an implantation assembly prior to and during the injecting the viscoelastic material. Additionally, the axial elongate hollow conduit is mounted onto an implantation assembly prior to and during the inserting of the intraocular lens into the viscoelastic material.

In accordance with a preferred embodiment of the present invention, in a first operative stage, haptics of an intraocular lens to be injected are located in recesses formed in an azimuthally precise mounting element forming part of the implantation assembly and a rearward portion of the intraocular lens is seated in a bore formed in the azimuthally precise mounting element.

Preferably, the axial elongate hollow conduit includes a first relatively rigid housing portion, which defines the syringe connector and a relatively flexible sleeve portion which is mounted onto the relatively rigid housing portion and is formed with a angled edge defining the second end of the axial elongate hollow conduit and in the first operative stage the angled edge lies adjacent the intraocular lens. Additionally, in a second operative stage, viscoelastic material is transferred into the interior of the flexible sleeve portion.

In accordance with a preferred embodiment of the present invention in a third operative stage the intraocular lens is axially displaced into the flexible sleeve and the haptics are positioned in a backward folded over orientation, while maintaining precise predetermined azimuthal positioning thereof relative to the longitudinal axis.

In accordance with a preferred embodiment of the present invention, in a further operative stage, the axial elongate hollow conduit is disengaged from the implantation assembly and connected to an implantation syringe.

BRIEF DESCRIPTION OF THE DRAWINGS

The present invention will be understood and appreciated more fully from the following detailed description, taken in conjunction with the drawings in which:

FIG. 2 is a simplified exploded view illustration of an implantation assembly forming part of the apparatus of FIG. 1;

FIGS. 5A, 5B, 5C and 5D are simplified respective rearward-facing and forward facing pictorial, rearward-facing planar and sectional view illustrations of an axial displacer guide element, forming part of the implantation assembly of FIG. 2, FIG. 5D being taken along lines 5D-5D in FIG. 5A;

FIGS. 14A, 14B, 14C and 14D are simplified respective forward-facing and rearward facing pictorial, pictorial sectional and planar sectional illustrations of the implantation assembly of FIG. 2 in a first operative orientation, FIGS. 14C & 14D being taken along lines 14C-14C in FIG. 14B;

FIGS. 15A and 15B are simplified respective pictorial and planar sectional illustrations of the implantation assembly of FIG. 2 in a second operative orientation upon completion of viscoelastic material injection, FIG. 15B being taken along lines 15B-15B in FIG. 15A;

FIGS. 16A and 16B are simplified respective pictorial sectional and planar sectional illustrations of the implantation assembly of FIG. 2 in its second operative orientation, as shown in FIGS. 15A & 15B, following completion of viscoelastic material injection and disengagement of a viscoelastic material syringe therefrom, FIGS. 16A and 16B being taken partially along lines 15B-15B in FIG. 15A;

FIGS. 17A and 17B are simplified respective pictorial sectional and planar sectional illustrations of the implantation assembly of FIG. 2 in its second operative orientation, as shown in FIGS. 15A-16B, following engagement of an implantation syringe thereto, FIGS. 17A and 17B being taken partially along lines 15B-15B in FIG. 15A;

FIGS. 18A and 18B are simplified respective pictorial sectional and planar sectional illustrations of the implantation assembly of FIG. 2 in a third operative orientation, FIGS. 18A and 18B being taken along the same plane as FIGS. 15A-17B;

FIGS. 19A and 19B are simplified respective pictorial and planar sectional illustrations of the implantation assembly of FIG. 2 in a fourth operative orientation, following removal of a safety catch therefrom, FIG. 19B being taken partially along lines 19B-19B in FIG. 19A.

DETAILED DESCRIPTION OF A PREFERRED EMBODIMENT

Figure 1:
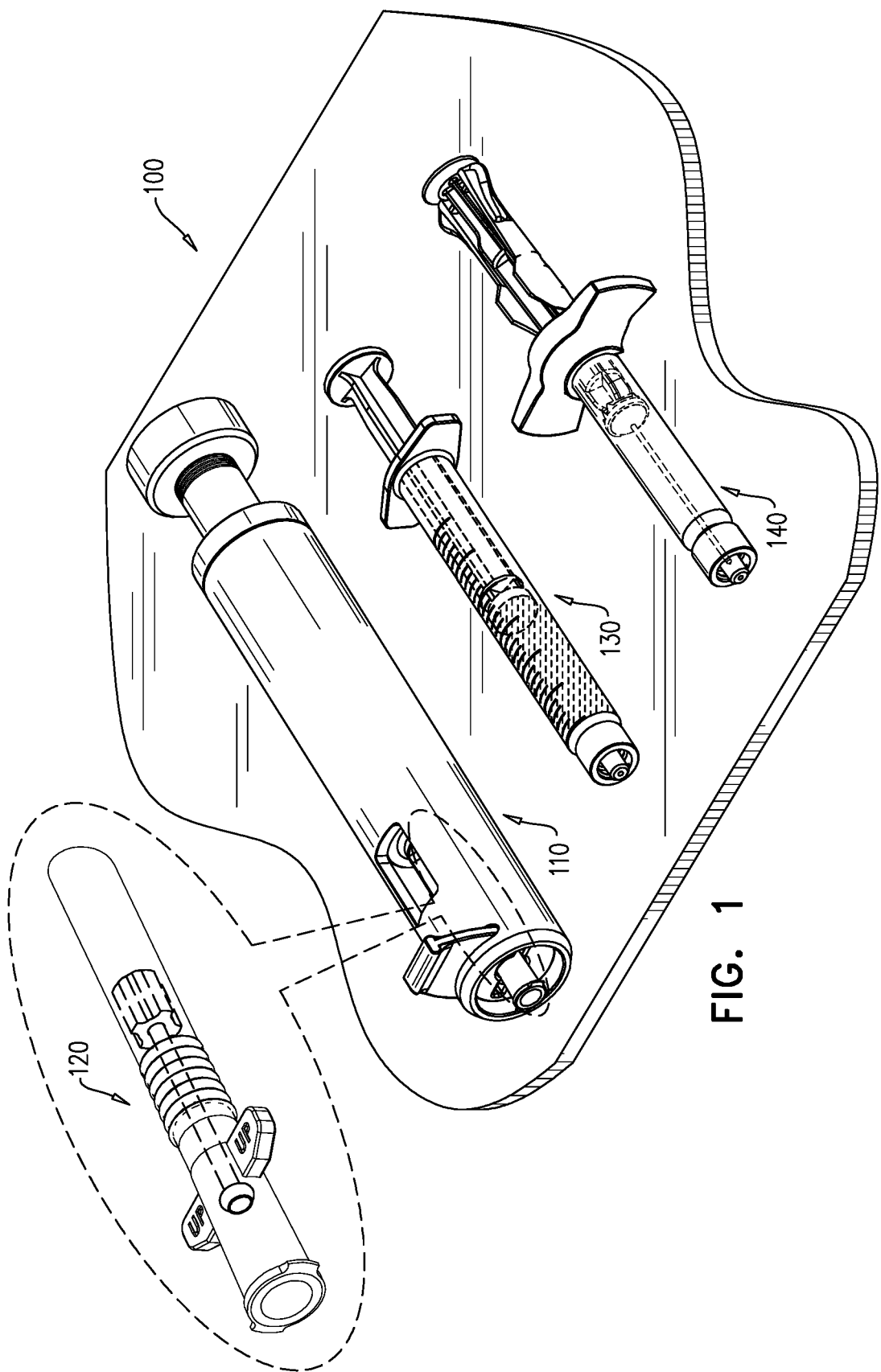
FIG. 1 is a simplified illustration of apparatus for use in implanting intraocular lenses, constructed and operative in accordance with a preferred embodiment of the present invention.

Reference is now made to FIG. 1, which is a simplified illustration of apparatus for use in implanting intraocular lenses 100, constructed and operative in accordance with a preferred embodiment of the present invention.

As seen in FIG. 1, the apparatus for use in implanting intraocular lenses 100 preferably includes an implantation assembly 110, which partially encloses an IOL implantation insertion assembly 120, a viscoelastic material-filled syringe 130 and an implantation syringe 140. Implantation assembly 110 is described in detail hereinbelow with reference to FIGS. 2-8B. IOL implantation insertion assembly 120 is described in detail hereinbelow with reference to FIGS. 9A-12. An example of a commercially available viscoelastic material-filled syringe 130 is filled with sodium hyaluronate, commercially available from Johnson & Johnson, under the product name HEALON® 5.

Reference is now made to FIG. 2, which is a simplified exploded view illustration of implantation assembly 110, forming part of the apparatus of FIG. 1. As seen in FIG. 2, implantation assembly 110 is generally arranged along a longitudinal axis 148 and preferably comprises a manually engageable axial displacer 150, a tip portion of which is enclosed by a displacing element 151, preferably formed of silicone. Manually engageable axial displacer 150 fixedly engages an internal cylindrical element 152.

Internal cylindrical element 152 is, in turn, located within a main housing element 154, which has a safety catch 155 removably associated therewith. Also located within main housing element 154 are a coil spring 156 and an axial displacer guide element 158. Seated at a rear end of main housing element 154 is a collar member 159, having a rearward facing surface 160. Located forwardly of axial displacer guide element 158 is an intraocular lens 161 and an azimuthally precise mounting element 162 therefor, which is preferably formed of silicone.

Intraocular lens 161 is preferably initially mounted onto azimuthally precise mounting element 162 and located within an IOL implantation insertion assembly housing element 164, which axially removably surrounds IOL implantation insertion assembly 120. IOL implantation insertion assembly 120 is initially and removably mounted onto IOL implantation insertion assembly housing element 164. As described hereinbelow in greater detail with reference to FIGS. 9A-12, IOL implantation insertion assembly 120 includes a housing element 170, a dual purpose elongate hollow tube in the form of a hollow pusher rod 172 slidably and sealingly disposed within housing element 170 by means of an O-ring 174, a pusher element 176 fixed to a rearward end of pusher rod 172 and a flexible sleeve 178, having a forward portion thereof fitted over a rearward portion of housing element 170.

Housing element 170 and flexible sleeve 178 define an axial elongate hollow conduit defining an intraocular lens injection pathway extending along longitudinal axis 148.

Figure 3A:
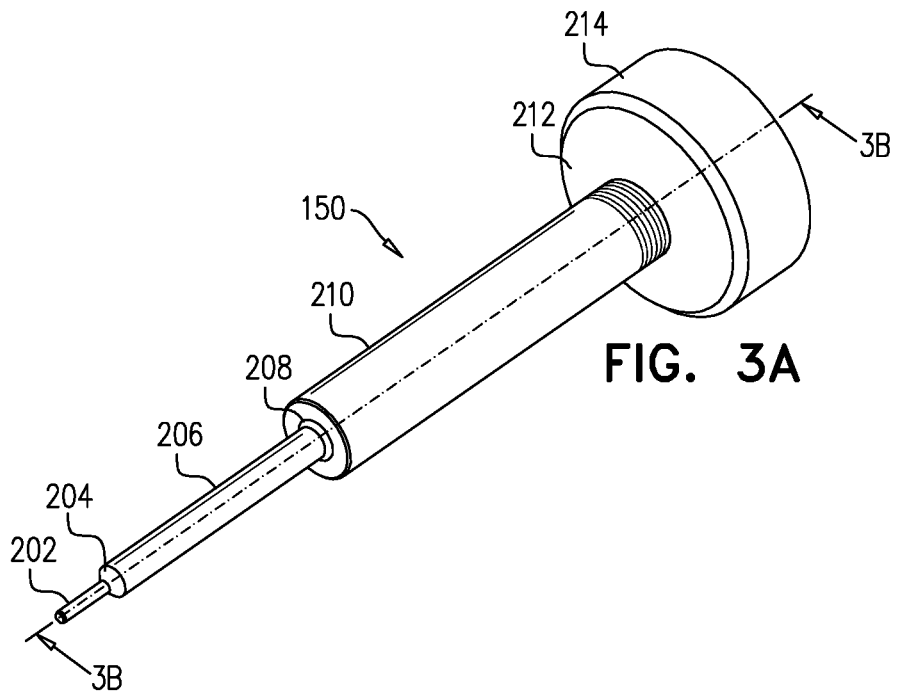
FIGS. 3A and 3B are simplified respective pictorial and sectional view illustrations of a manually engageable axial displacer, forming part of the implantation assembly of FIG. 2, FIG. 3B being taken along lines 3B-3B in FIG. 3A.
Figure 3B:
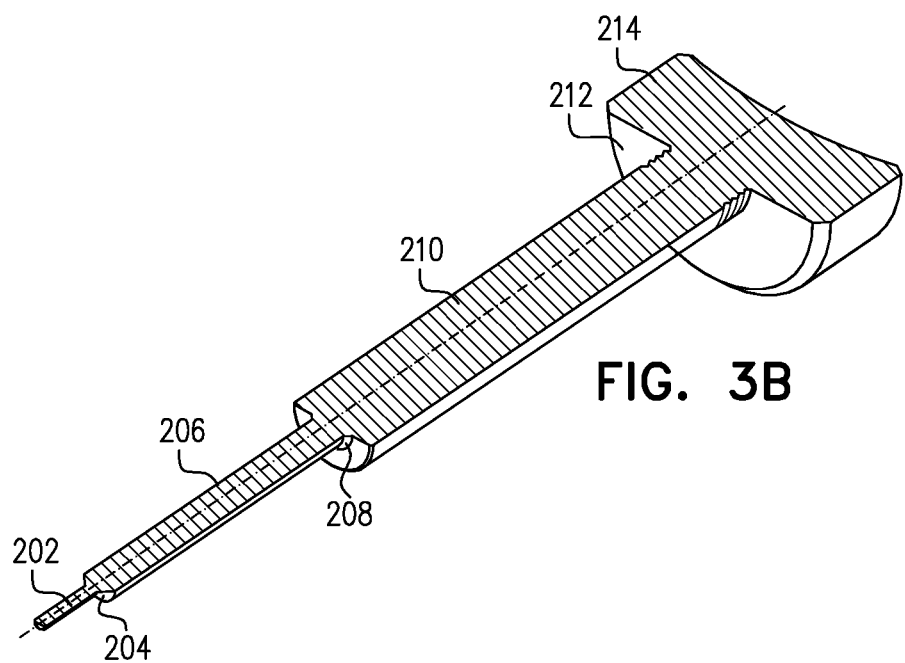

Reference is now made to FIGS. 3A and 3B, which are simplified respective pictorial and sectional view illustrations of manually engageable axial displacer 150, forming part of the implantation assembly 110 of FIG. 2, FIG. 3B being taken along lines 3B-3B in FIG. 3A. As seen in FIGS. 3A and 3B, manually engageable axial displacer 150 is preferably an axially symmetric unitary element and comprises a forward generally cylindrical pin portion 202, terminating rearwardly at a tapered portion 204 followed by a forward intermediate cylindrical portion 206, having a radius larger than that of forward generally cylindrical pin portion 202. Forward intermediate cylindrical portion 206 terminates rearwardly at a tapered portion 208 followed by a rearward intermediate cylindrical portion 210, having a radius larger than that of forward intermediate cylindrical pin portion 206. Rearward intermediate cylindrical portion 210 terminates at a forward-facing annular surface 212 of a rearward knob portion 214.

Figure 4A:
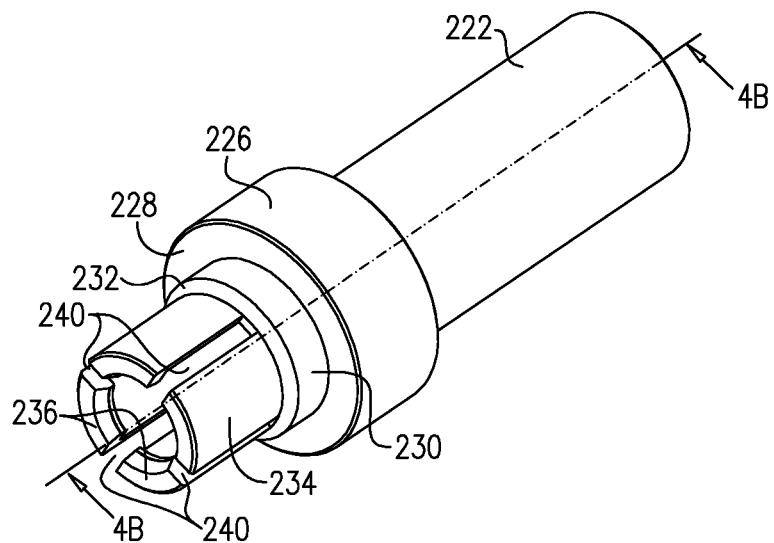
FIGS. 4A and 4B are simplified respective pictorial and sectional view illustrations of an internal cylindrical element, forming part of the implantation assembly of FIG. 2, FIG. 4B being taken along lines 4B-4B in FIG. 4A.
Figure 4B:
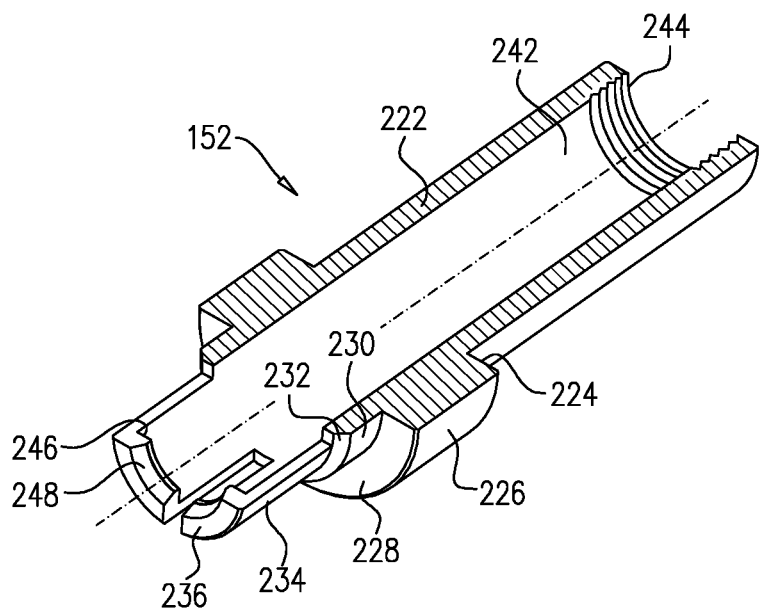

Reference is now made to FIGS. 4A and 4B, which are simplified respective pictorial and sectional view illustrations of internal cylindrical element 152, forming part of the implantation assembly of FIG. 2, FIG. 4B being taken along lines 4B-4B in FIG. 4A.

As seen in FIGS. 4A & 4B, internal cylindrical element 152 is preferably an axially symmetric unitary element and comprises a rearward generally cylindrical surface portion 222, which terminates forwardly at a rearward-facing annular surface 224. Rearward-facing annular surface 224 extends radially outwardly to a rearward intermediate generally cylindrical surface portion 226, having a radius larger than that of rearward generally cylindrical surface portion 222. Rearward intermediate generally cylindrical surface portion 226 extends forwardly to a forward-facing annular surface 228, which extends radially inwardly to a forward intermediate generally cylindrical surface portion 230, having a radius which is generally the same as that of rearward generally cylindrical surface portion 222. Forward intermediate generally cylindrical surface portion 230 extends forwardly to a forwardly and inwardly tapered surface portion 232, which terminates forwardly at a forward generally cylindrical surface portion 234, which terminates in a forward annular surface 236.

Forward generally cylindrical surface portion 234 is preferably formed with four, equally azimuthally distributed axial slots 240 which extend through forward generally cylindrical surface portion 234.

Internal cylindrical element 152 is preferably formed with a bore 242 of uniform radius, which extends from an open rear edge 244 of rearward generally cylindrical surface portion 222 to a rearward-facing annular surface 246 adjacent a forward end of forward generally cylindrical surface portion 234. Rearward-facing annular surface 246 extends inwardly to a forwardly and outwardly tapered circular surface 248, which terminates at forward annular surface 236.

Reference is now made to FIGS. 5A, 5B, 5C and 5D, which are simplified respective rearward-facing and forward facing pictorial, rearward-facing planar and sectional view illustrations of axial displacer guide element 158, forming part of the implantation assembly of FIG. 2, FIG. 5D being taken along lines 5D-5D in FIG. 5A.

As seen in FIGS. 5A-5D, axial displacer guide element 158 is preferably an axially symmetric unitary element having a uniform axial bore 250 and comprises a rearward-facing annular surface 260, which extends outwardly to rearward generally forwardly and outwardly tapered circumferential surface 262. Rearward generally forwardly and outwardly tapered circumferential surface 262 terminates forwardly in a forwardly-facing annular surface 264, which extends radially inwardly and terminates at a rearward cylindrical surface 266. Rearward cylindrical surface 266 terminates at a rearwardly-facing annular surface 268, which extends radially outwardly and terminates at a rearward intermediate cylindrical surface 270.

Rearward intermediate cylindrical surface 270 terminates at a rearwardly-facing annular surface 272, which extends radially outwardly and terminates at an intermediate cylindrical surface 274. Intermediate cylindrical surface 274 terminates at a circumferentially stepped forwardly-facing annular surface 276, which extends radially inwardly and terminates at a forwardly and inwardly tapered surface 278. Tapered surface 278 extends radially inwardly and terminates at a forward cylindrical surface 280. Forward cylindrical surface 280 terminates at a forwardly-facing annular surface 282.

Intermediate cylindrical surface 274 is preferably formed with three uniformly azimuthally spaced recesses 284. Each of recesses 284 has a curved outer surface including a rearward portion 286 of a first depth, an intermediate portion 288 of a second depth, less than the first depth and a forward portion 290 of a third depth, greater than the first depth.

Figure 6A:
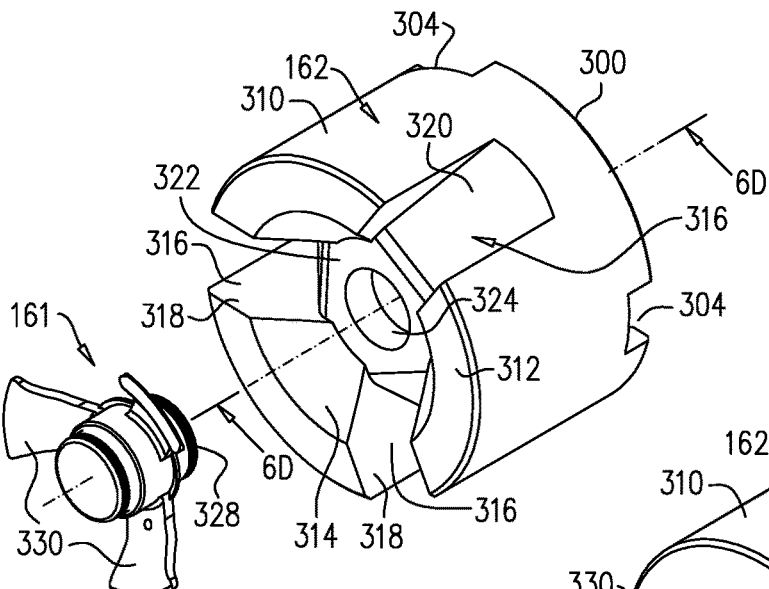
FIGS. 6A, 6B, 6C and 6D are simplified respective exploded and assembled rearward-facing pictorial, rearward-facing planar and partial sectional view illustrations of intraocular lens and an azimuthally precise mounting therefor, forming part of the implantation assembly of FIG. 2, FIG. 6D being taken along lines 6D-6D in FIG. 6A.
Figure 6B:
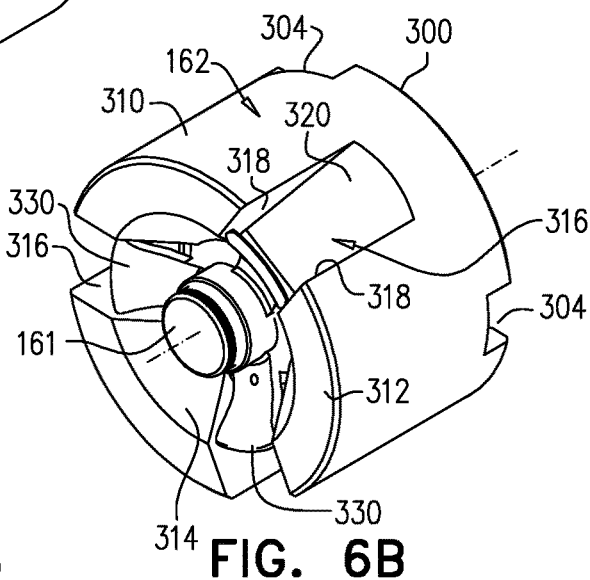
Figure 6C:
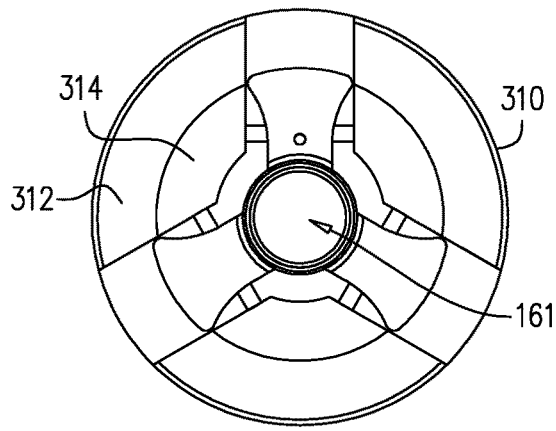
Figure 6D:
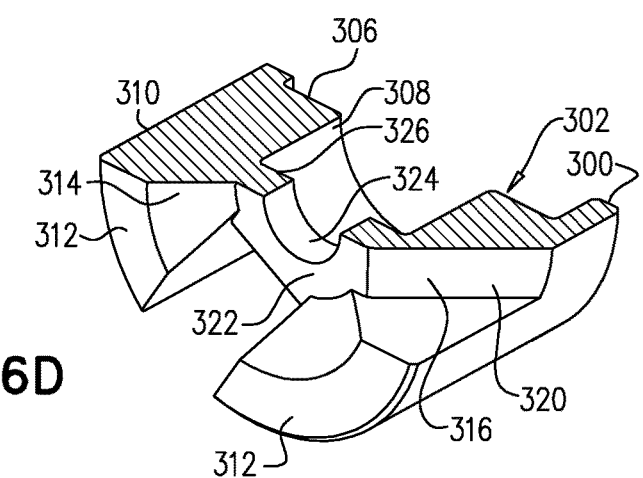

Reference is now made to FIGS. 6A, 6B, 6C and 6D, which are simplified respective exploded and assembled rearward-facing pictorial, rearward-facing planar and partial sectional view illustrations of intraocular lens 161 and azimuthally precise mounting element 162, forming part of the implantation assembly of FIG. 2, FIG. 6D being taken along lines 6D-6D in FIG. 6A.

As seen in FIG. 6A, intraocular lens 161 may be any suitable intraocular lens and is preferably a PR00035-00 IOL commercially available from Visioncare Ophthalmic Technologies, Inc.

As seen in FIGS. 6A-6D, azimuthally precise mounting element 162 is preferably an axially symmetric unitary element and comprises a rearward-facing annular surface 300, which surrounds a rearwardly-facing central recess 302 and is formed with three uniformly azimuthally separated cut outs 304. Central recess 302 is formed with a rearward-facing annular surface 306, which surrounds an axial bore 308.

Azimuthally precise mounting element 162 is formed with a radially outward-facing cylindrical surface 310, which terminates in a forwardly-facing annular surface 312, which extends inwardly to a rearwardly and inwardly tapered surface 314. Three uniformly azimuthally separated recesses 316 are formed in surfaces 310, 312 and 314, each recess 316 being defined by a pair of mutually parallel side surfaces 318 and by a rearwardly and outwardly tapered planar surface 320 extending rearwardly to cylindrical surface 310. Each of tapered planar surfaces 320 extends radially outwardly and rearwardly from a common forwardly-facing surface 322.

A central axial bore 324, which is narrower than bore 308, extends rearwardly from forwardly-facing surface 322 to a rearwardly-facing surface 326, parallel to surface 322, which defines a forward termination of axial bore 308 and a junction of bores 308 and 324.

As seen in FIGS. 6A and 6B, IOL 161 is preferably seated within azimuthally precise mounting element 162, with a rearward portion 328 of the IOL 161 being securely seated in bore 324 and its haptics 330 being located in, but not seated in, respective recesses 316.

Figure 7A:
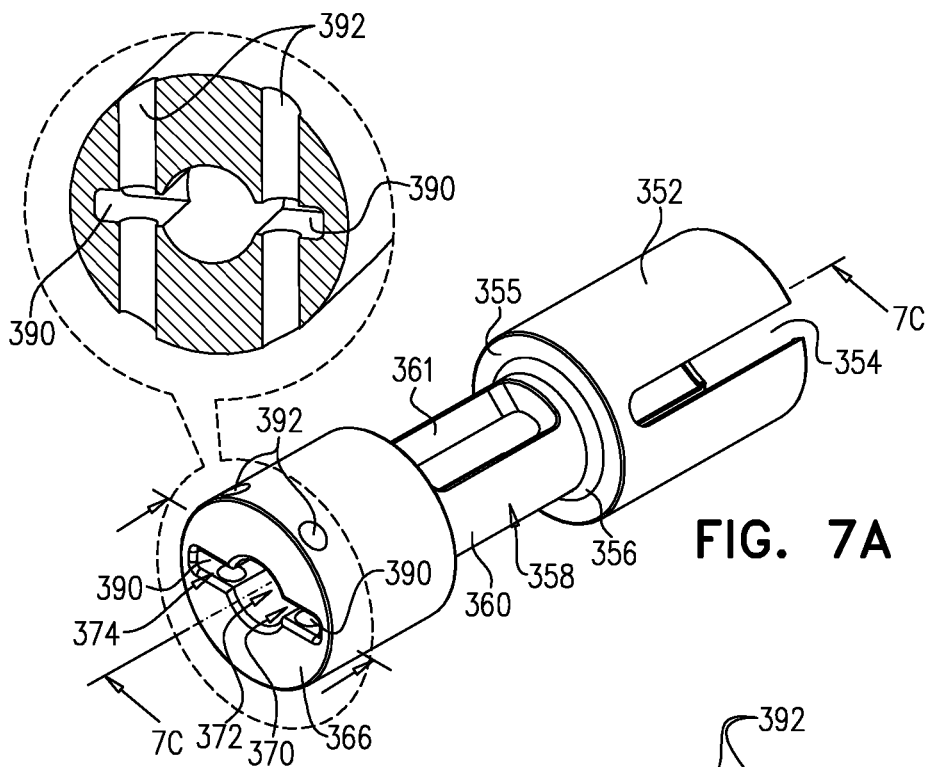
FIGS. 7A, 7B and 7C are simplified respective rearward-facing and forward facing pictorial and sectional view illustrations of an Intraocular Lens (IOL) implantation insertion assembly housing element, forming part of the implantation assembly of FIG. 2, FIG. 7C being taken along lines 7C-7C in FIG. 7A.
Figure 7B:
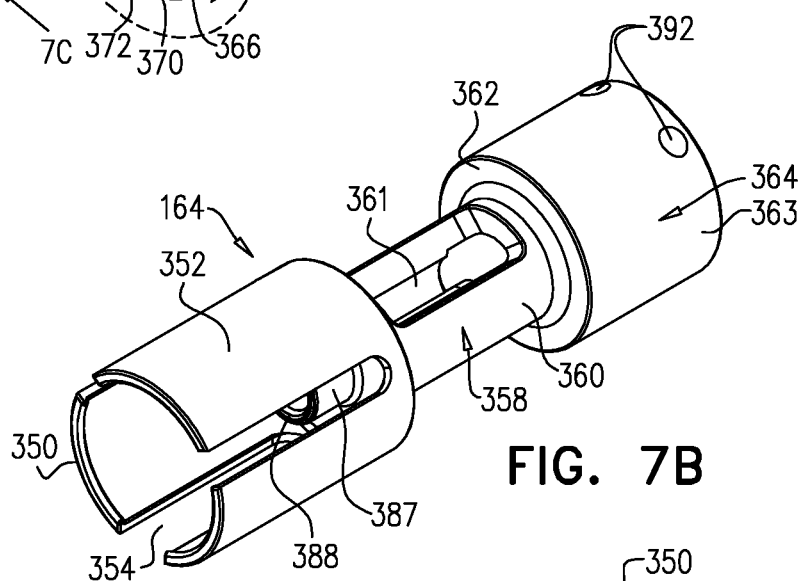
Figure 7C:
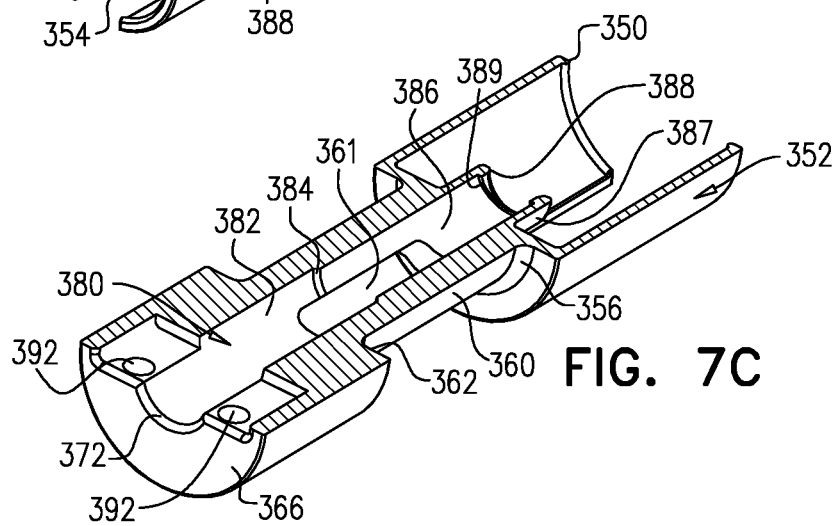

Reference is now made to FIGS. 7A, 7B and 7C, which are simplified respective rearward-facing and forward-facing pictorial and sectional view illustrations of IOL implantation insertion assembly housing element 164, forming part of the implantation assembly of FIG. 2, FIG. 7C being taken along lines 7C-7C in FIG. 7A.

As seen in FIGS. 7A-7C, IOL implantation insertion assembly housing element 164 is preferably an axially side-to-side symmetric unitary element and comprises a rearward-facing annular surface 350, which extends radially outwardly to a hollow rearward cylindrical portion 352 having formed therein three uniformly azimuthally distributed axial slits 354. Cylindrical portion 352 terminates forwardly at a forwardly facing annular surface 355, which extends radially inwardly to a forwardly and inwardly tapered surface 356, which in turn terminates forwardly in an intermediate cylindrical portion 358, which defines a radially outwardly directed cylindrical surface 360, formed with a pair of axial slots 361.

Cylindrical surface 360 terminates forwardly at a rearwardly directed annular surface 362, which extends radially outwardly to an outwardly directed cylindrical surface 363 of a forward cylindrical portion 364, having a forward-facing planar surface 366. Forward-facing planar surface 366 is formed with a key-hole type opening 370 including a generally circular central portion 372 and a pair of generally rectangular side portions 374.

Extending rearwardly from forward-facing planar surface 366 at generally circular central portion 372 is an axial bore 380, including a first portion 382, which extends to a tapered shoulder 384 interior of intermediate cylindrical portion 358, and a second portion 386, slightly narrower than first portion 382, which extends rearwardly from shoulder 384 to a cylindrical portion 387, located within hollow rearward cylindrical portion 352, at a rearward end of which is formed a smoothly rounded edge 388. Forwardly of edge 388 there is formed an angled interior shoulder 389.

Extending rearwardly from forward-facing planar surface 366 at generally rectangular side portions 374 are a pair of generally planar rectangular recesses 390, each of which is transversed by a throughgoing bore 392.

Figure 8A:
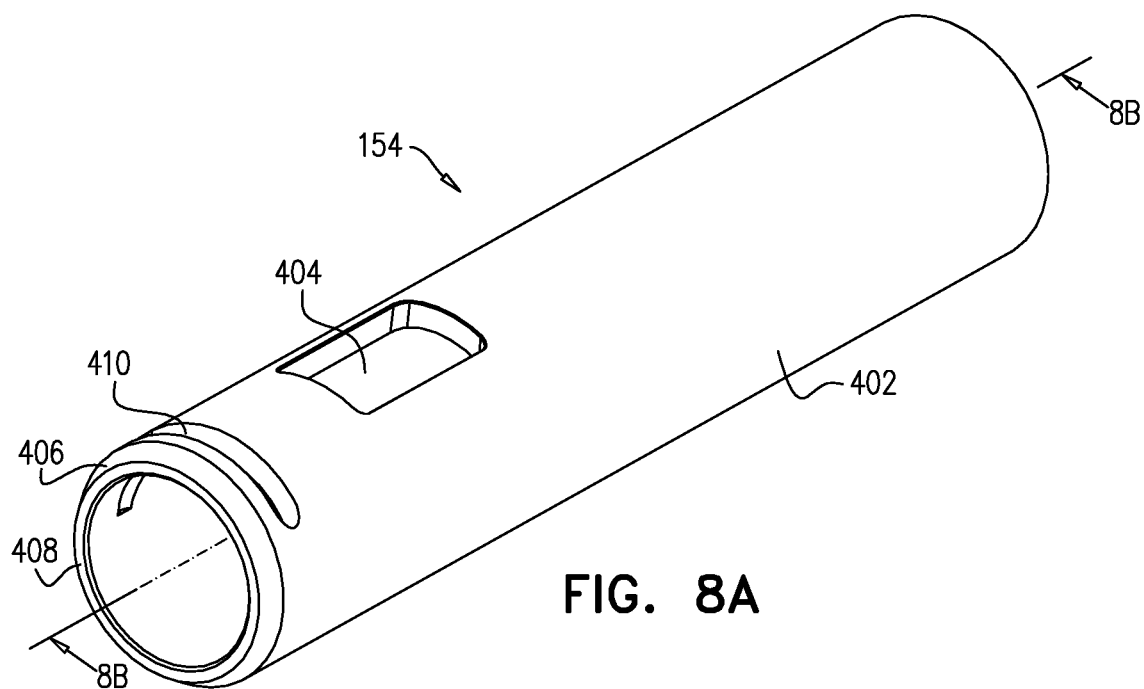
FIGS. 8A and 8B are simplified respective pictorial and sectional view illustrations of a main housing element, forming part of the implantation assembly of FIG. 2, FIG. 8B being taken along lines 8B-8B in FIG. 8A.
Figure 8B:
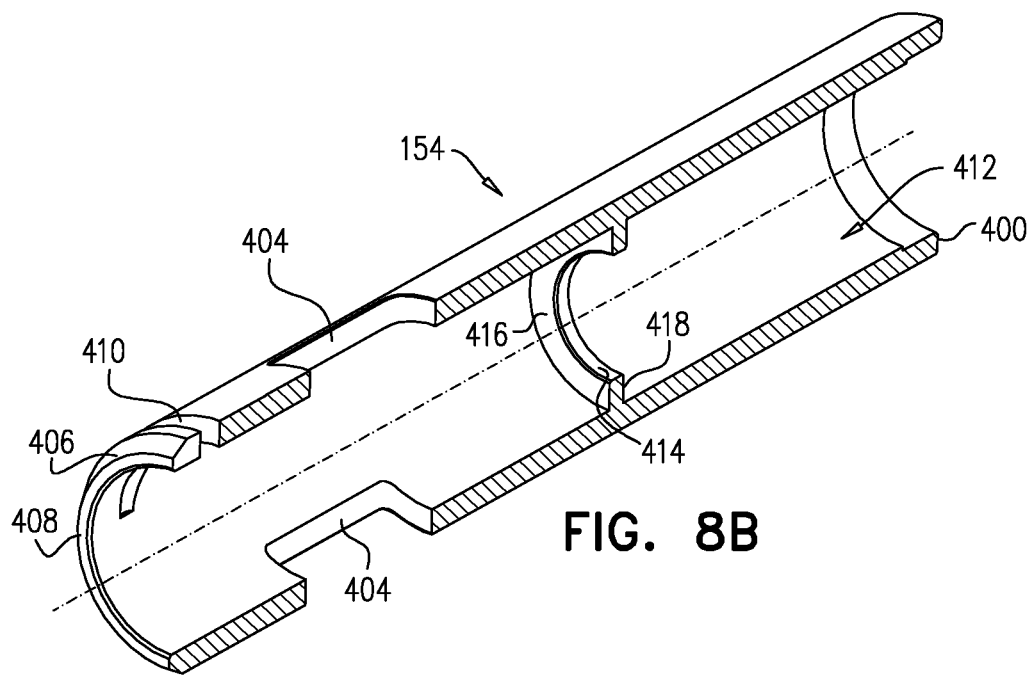

Reference is now made to FIGS. 8A and 8B, which are simplified respective pictorial and sectional view illustrations of main housing element 154, forming part of the implantation assembly of FIG. 2, FIG. 8B being taken along lines 8B-8B in FIG. 8A. As seen in FIGS. 8A and 8B, main housing element 154 is preferably an axially side-to-side symmetric unitary element and comprises a rearward-facing annular surface 400, which extends radially outwardly to a cylindrical surface 402 having formed therein a pair of cut outs 404. Cylindrical surface 402 terminates forwardly at a forwardly and inwardly tapered surface 406, which extends to an annular forward-facing surface 408. A partially circumferential slot 410 is located rearwardly of tapered surface 406. Main housing element 154 is formed with an axial bore 412, which is interrupted by an internal radially inwardly extending ring 414 defining a forward facing annular surface 416 and a rearward-facing annular surface 418.

Figure 9A:
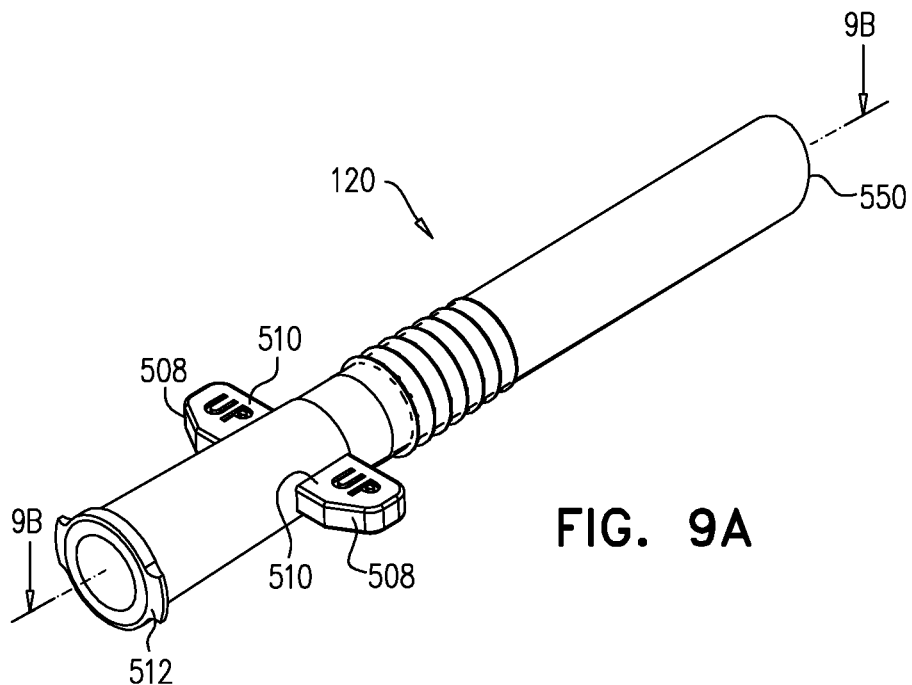
FIGS. 9A, 9B and 9C are simplified respective pictorial, planar sectional and exploded view illustrations of an IOL implantation insertion assembly forming part of the apparatus of FIG. 1, FIG. 9B being taken along lines 9B-9B in FIG. 9A.
Figure 9B:
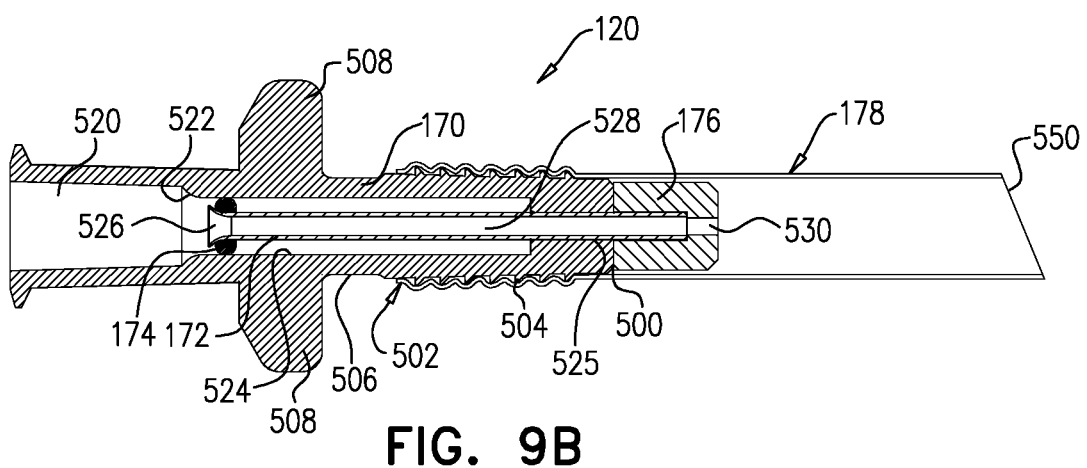
Figure 9C:
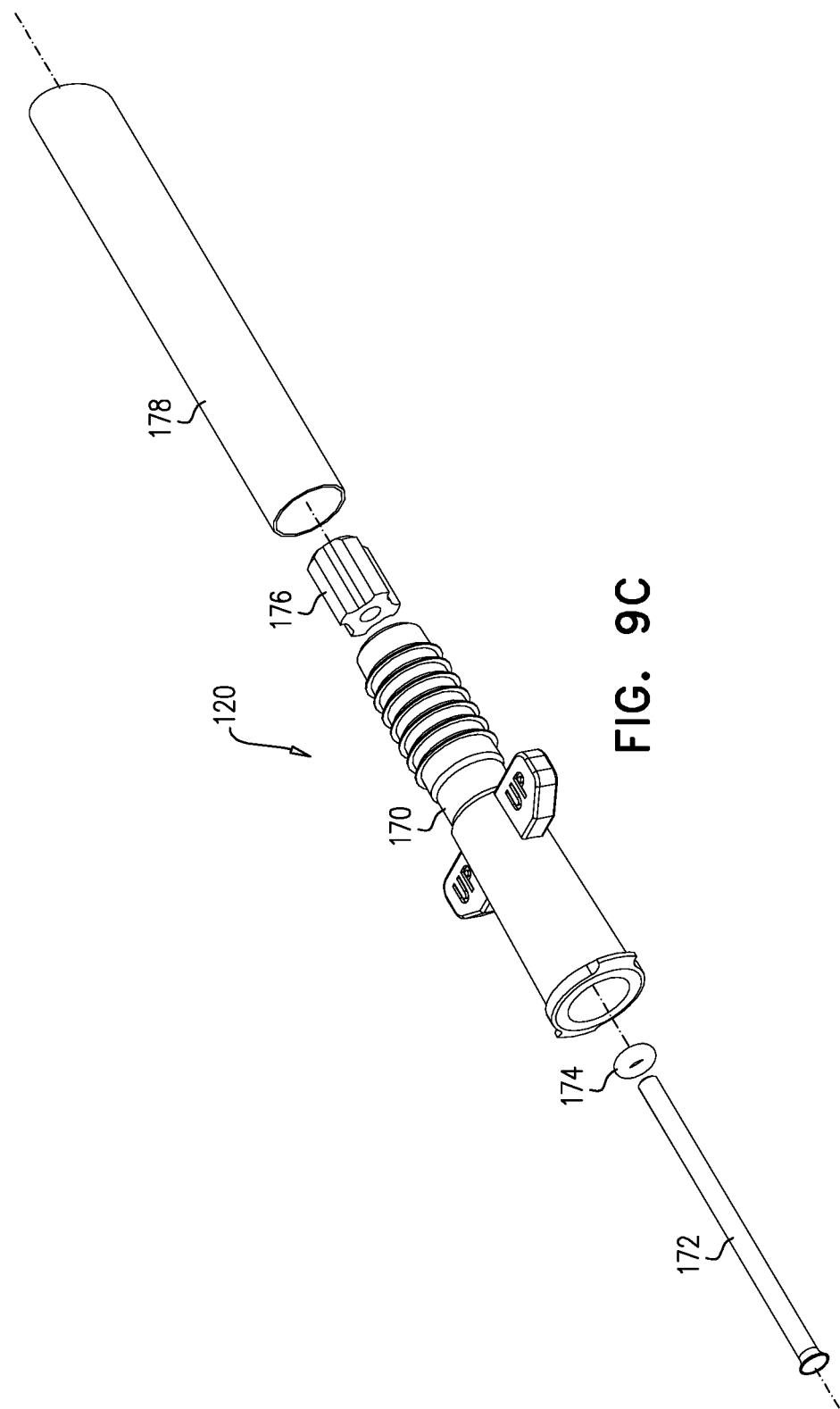
Figure 10A:
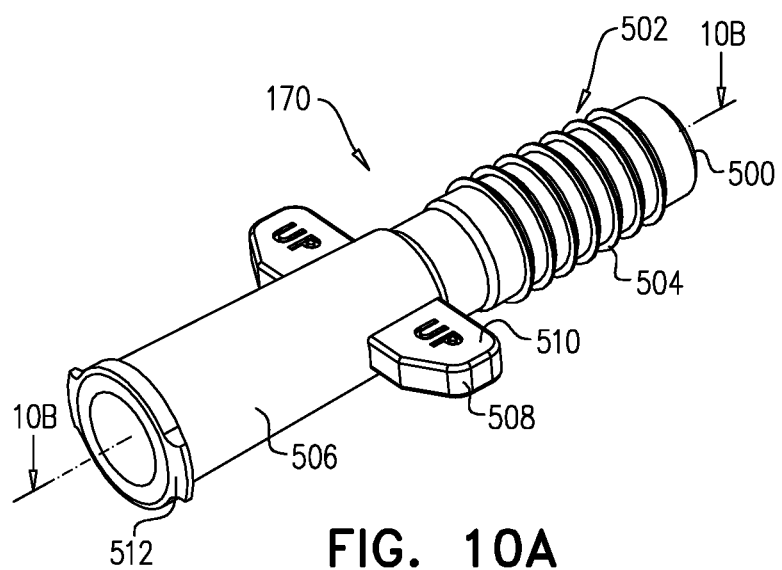
FIGS. 10A and 10B are simplified respective pictorial and sectional illustrations of a portion of the IOL implantation insertion assembly of FIGS. 9A-9C, FIG. 10B being taken along lines 10B-10B in FIG. 10A.
Figure 10B:
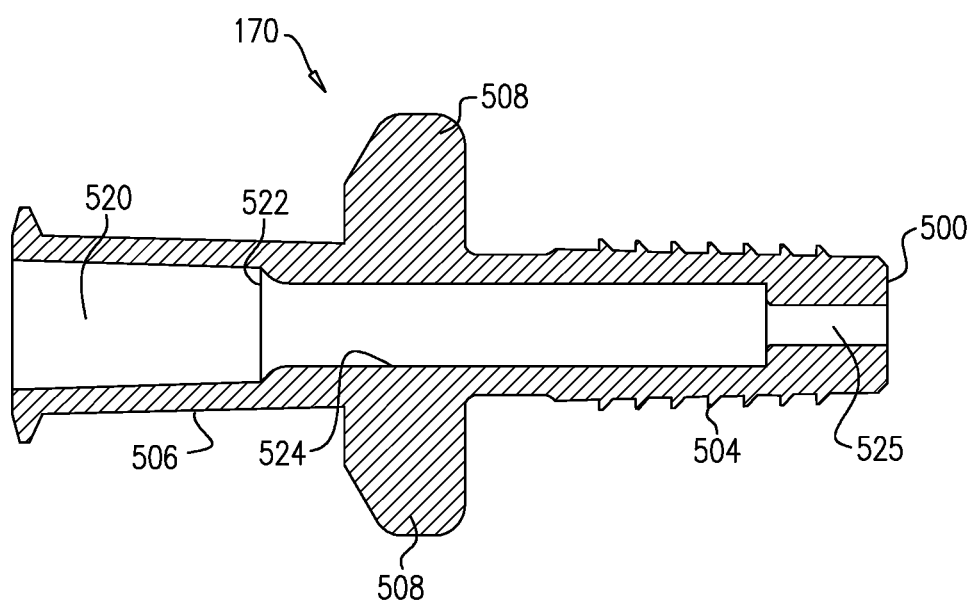
Figure 11:
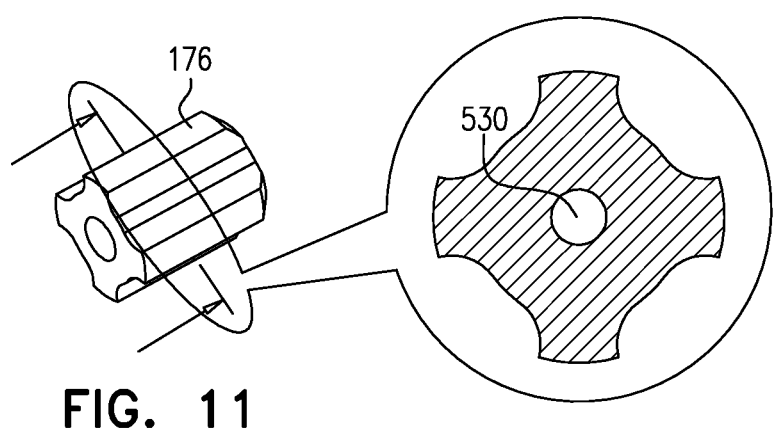
FIG. 11 is a simplified pictorial and sectional illustration of another portion of the IOL implantation insertion assembly of FIGS. 9A-9C.
Figure 12:
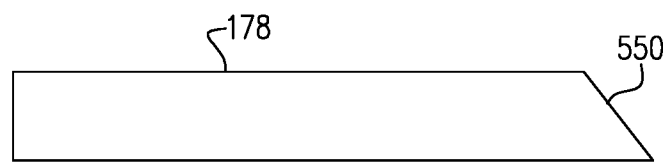
FIG. 12 is a simplified planar side view illustration of a further portion of the IOL implantation insertion assembly of FIGS. 9A-9C.

Reference is now made to FIGS. 9A-9C, which are simplified respective pictorial, planar sectional and exploded view illustrations of IOL implantation insertion assembly 120 forming part of the apparatus of FIG. 1, to FIGS. 10A and 10B, which are simplified respective pictorial and sectional illustrations of a portion of the IOL implantation insertion assembly 120 of FIGS. 9A-9C, to FIG. 11, which is a simplified pictorial and sectional illustration of another portion of the IOL implantation insertion assembly 120 of FIGS. 9A-9C, and to FIG. 12, which is a simplified planar side view illustration of a further portion of the IOL implantation insertion assembly 120 of FIGS. 9A-9C.

As noted above in the description of FIG. 2, IOL implantation insertion assembly 120 includes a relatively rigid housing element 170, a hollow pusher rod 172, slidably and sealingly disposed within housing element 170 by means of an O-ring 174, a pusher element 176 fixed to a rearward end of pusher rod 172 and a relatively flexible sleeve 178 having a forward portion thereof fitted over a preferably ribbed rearward portion of housing element 170.

As seen in FIGS. 9A-12, housing element 170 is preferably an axially side-to-side symmetric unitary element and comprises a rearward-facing annular surface 500, which extends radially outwardly to a cylindrical surface 502, including a ribbed rearward portion 504 and a generally smooth forward portion 506. Extending outwardly from generally smooth forward portion 506 are a pair of generally flat wing portions 508, one surface 510, preferably having a user visible designation such as "UP". Forward portion 506 terminates at a forward end thereof in a conventional syringe connector, preferably a luer lock connector 512, suitable for engagement therewith by a syringe having a conventional luer connector, such as syringes 130 and 140 (FIG. 1). Wing portions 508 are important for enabling an implanter to easily precisely fixate the haptics 330 of the IOL 161 during implantation.

Housing element 170 is formed at a forward end thereof with a slightly tapered bore 520, which narrows rearwardly at a tapered location 522 to a cylindrical bore 524, which terminates in a relatively narrow cylindrical bore 525.

Hollow pusher rod 172 is formed with a fluid entry end in the form of a tapered opening 526, which communicates with a throughgoing cylindrical bore 528. Hollow pusher rod 172 is initially fully seated in cylindrical bore 524 and sealed with respect thereto by O-ring 174. Hollow pusher rod 172 slidingly extends through cylindrical bore 525 and is fixed to pusher element 176, which is, in turn, formed with a cylindrical bore 530, which communicates with bore 528 of hollow pusher rod 172.

A forward end of flexible sleeve 178 is tightly fitted over ribbed rearward portion 504 and flexible sleeve 178 extends rearwardly beyond rearward-facing annular surface 500 and terminates in a tapered rearward facing edge 550. It is appreciated that the mutual orientation of wing portions 508 and the angled edge 550 is as shown in FIG. 9B, such that the angular orientation of angled edge 550 matches the angular orientation of tapered shoulder 389 of IOL implantation insertion assembly housing element 164, when IOL implantation insertion assembly 120 is fully seated in its required aximuthal orientation with respect to IOL implantation insertion assembly housing element 164.

It is appreciated that hollow pusher rod 172 is displaceable along longitudinal axis 148 (FIG. 2) relative to housing element 170 and is operative, when rearwardly displaced, to rearwardly displace pusher element 176 towards tapered rearward facing edge 550.

Figure 13A:
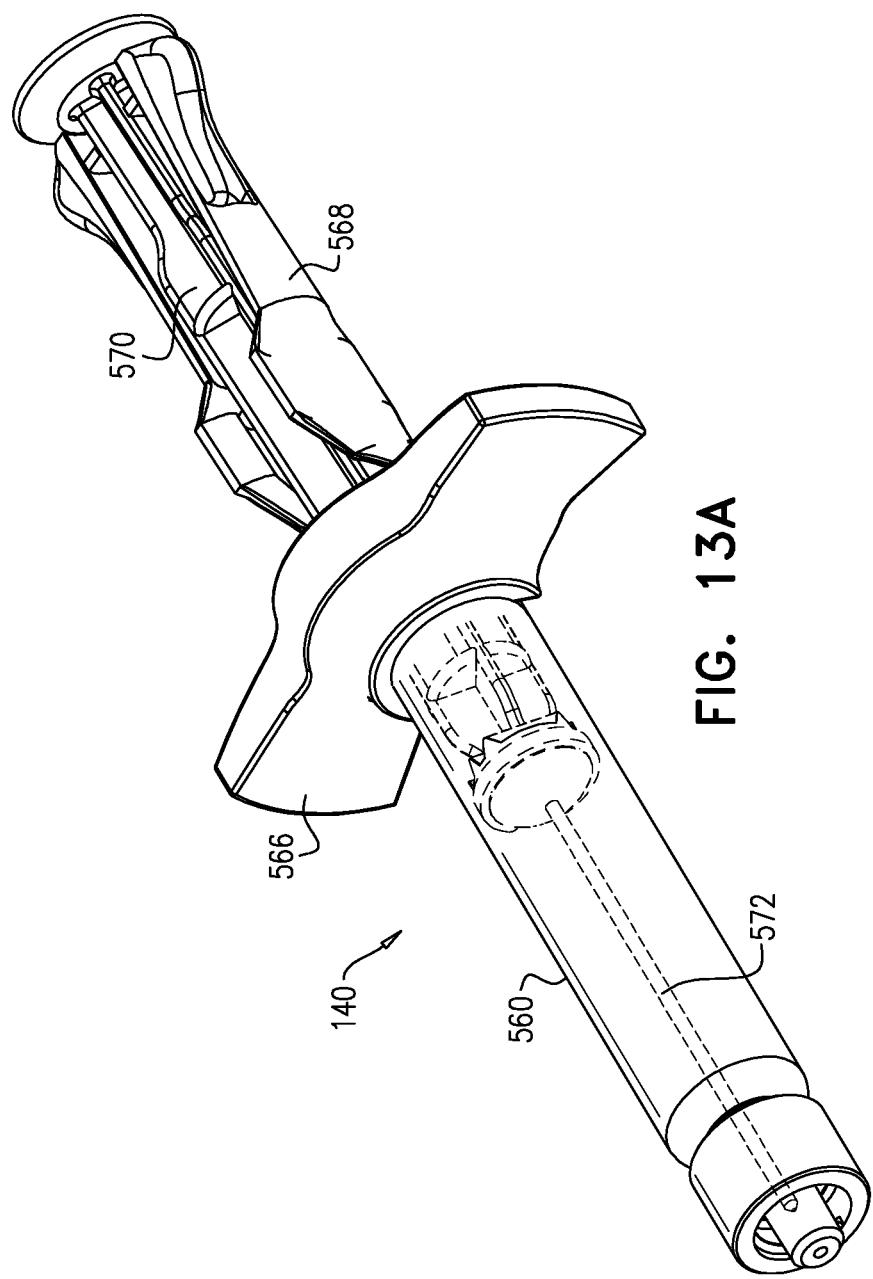
FIGS. 13A and 13B are simplified respective pictorial assembled and exploded view illustrations of an implantation syringe, which forms part of the apparatus of FIG. 1.
Figure 13B:
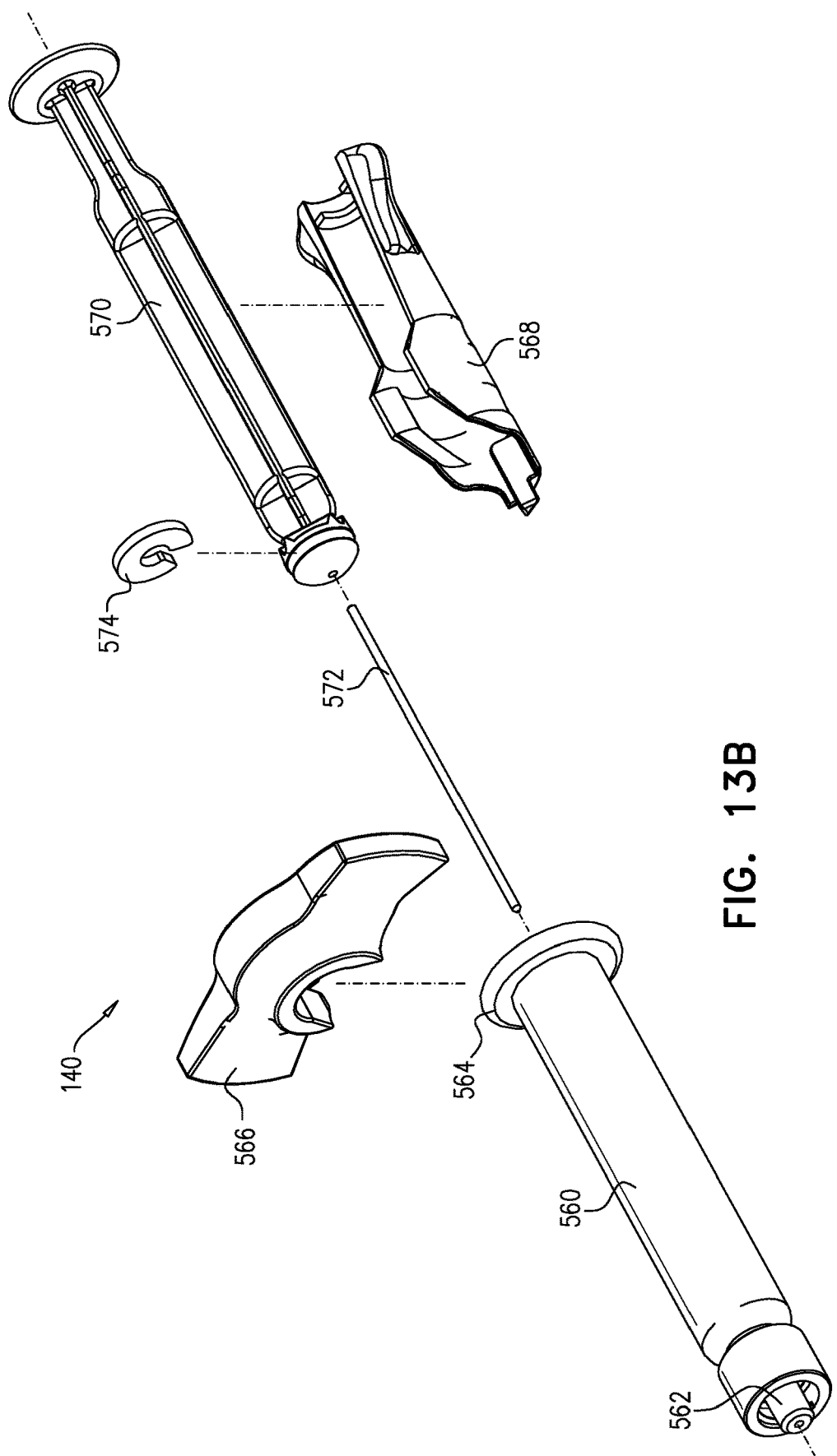
Figure 14C:
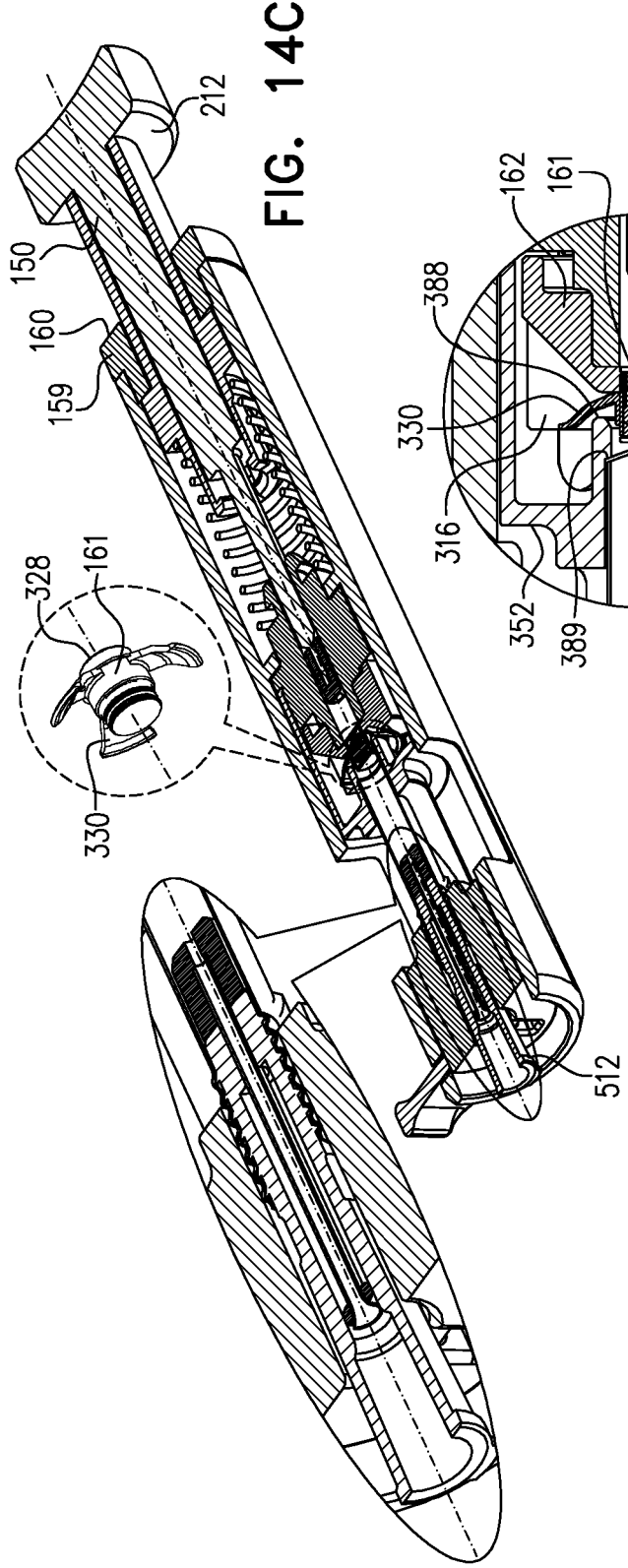
Figure 14D:
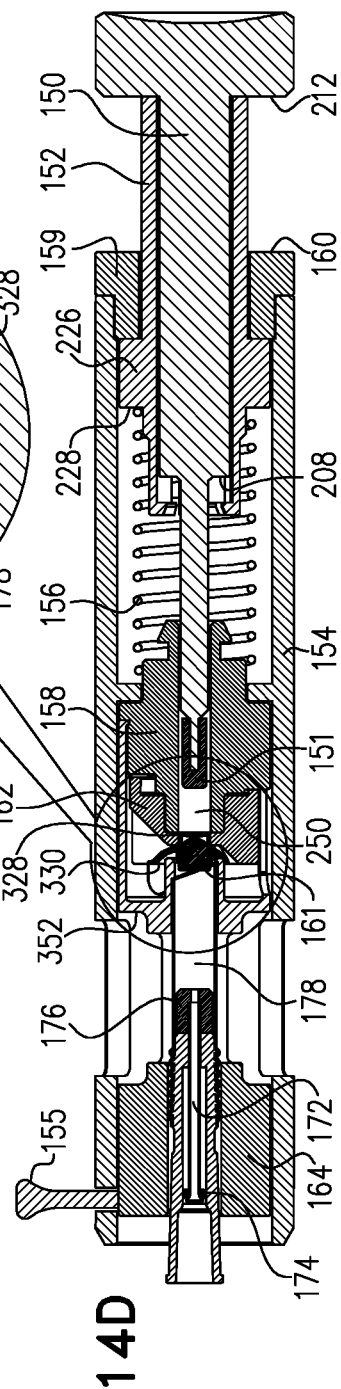

Reference is now made to FIGS. 13A and 13B, which illustrate implantation syringe 140. It is appreciated that any suitable implantation syringe may alternatively be employed. As seen in FIGS. 13A & 13B, implantation syringe 140 preferably includes a cylindrical barrel portion 560 having a narrow forward opening 562 and a rearward flange 564. A retaining portion 566 is rotatably mounted on rearward flange 564 to assist in required proper orientation of the IOL implantation insertion assembly 120 during implantation.

Rearward of barrel portion 560 is a removable stop element 568, which prevents inadvertent axial displacement of a manually axially displaceable pusher element 570, forwardly of which is mounted a pusher rod 572, which is configured to be selectably axially displaced through narrow forward opening 562. A notched positioning ring catch 574 non-sealingly engages pusher element 570 and housing portion 568 to guide pusher element 570 during its axial displacement through barrel portion 560.

Reference is now made to FIGS. 14A-14D, which illustrate the implantation assembly of FIG. 2 in a first operative orientation, which typically is an "out of the box" operative orientation. It is seen that rearward portion 328 of IOL 161 is seated in bore 324 (FIGS. 6A-6D) of azimuthally precise mounting element 162. It is also seen that haptics 330 of IOL 161 are located in, but not seated in, recesses 316 (FIGS. 6A-6D) of azimuthally precise mounting element 162, as shown in FIG. 6B. In this orientation, tapered rearward facing edge 550 of flexible sleeve 178 lies adjacent shoulder 389 of IOL implantation insertion assembly housing element 164 and adjacent IOL 161. In this operative orientation, manually engageable axial displacer 150 is maintained in a retracted orientation under urging of coil spring 156, such that forward-facing annular surface 212 of manually engageable axial displacer 150 is rearwardly spaced from rearward facing surface 160 of collar member 159. Flexible sleeve 178 is in fluid communication with hollow pusher rod 172. Smoothly rounded edge 388 preferably is not in touching engagement with haptics 330 of IOL 161.

Reference is now made to FIGS. 15A and 15B, which are simplified respective pictorial and planar sectional illustrations of the implantation assembly of FIG. 2 in a second operative orientation following attachment of viscoelastic material-filled syringe 130 and injection of viscoelastic material into sleeve 178.

As seen in FIGS. 15A and 15B, viscoelastic material-filled syringe 130 is connected to luer lock connector 512 of forward portion 506 of housing element 170. Viscoelastic material 900 contained therein is transferred through hollow pusher rod 172 into the interior of flexible sleeve 178 and into portions of hollow rearward cylindrical portion 352, forward of azimuthally precise mounting element 162, thereby surrounding IOL 161. Smoothly rounded edge 388 preferably is still not in touching engagement with haptics 330 of IOL 161.

Reference is now made to FIGS. 16A and 16B, which are simplified respective pictorial sectional and planar sectional illustrations of the implantation assembly of FIG. 2 in its second operative orientation, as shown in FIGS. 15A & 15B, following injection of viscoelastic material 900 and disengagement of viscoelastic material-filled syringe 130 therefrom.

Reference is now made to FIGS. 17A and 17B, which are simplified respective pictorial sectional and planar sectional illustrations of the implantation assembly of FIG. 2 in its second operative orientation, as shown in FIGS. 16A & 16B, following engagement of implantation syringe 140 thereto.

Reference is now made to FIGS. 18A and 18B, which are simplified respective pictorial sectional and planar sectional illustrations of the implantation assembly of FIG. 2 in a third operative orientation, FIGS. 18A and 18B being taken along the same plane as FIGS. 15B-17B.

As seen in FIGS. 18A and 18B, following attachment of implantation syringe 140, rearward knob portion 214 of manually engageable axial displacer 150 is depressed by a user, thereby compressing coil spring 156. Forward movement of manually engageable axial displacer 150 causes displacing element 151 to engage rearward portion 328 of IOL 161 and forwardly displace IOL 161 from azimuthally precise mounting element 162 into flexible sleeve 178. Forward movement of IOL 161 towards flexible sleeve 178 causes haptics 330 to engage smoothly rounded edge 388, which engagement gently folds the haptics 330 rearwardly into a backwardly folded over orientation as seen in enlargement A of FIG. 18B.

Continued forward movement of IOL 161 past edge 388 brings IOL 161 past shoulder 389 of IOL implantation insertion assembly housing element 164, and past edge 550 of flexible sleeve 178, towards pusher element 176, to a final loaded position within IOL implantation insertion assembly 120.

As seen in enlargement B of FIG. 18B, forwardly-facing annular surface 264 of axial displacer guide element 158 lockingly engages rearward-facing annular surface 246 of internal cylindrical element 152 to ensure precise positioning of IOL 161 within flexible sleeve 178.

Figure 20:
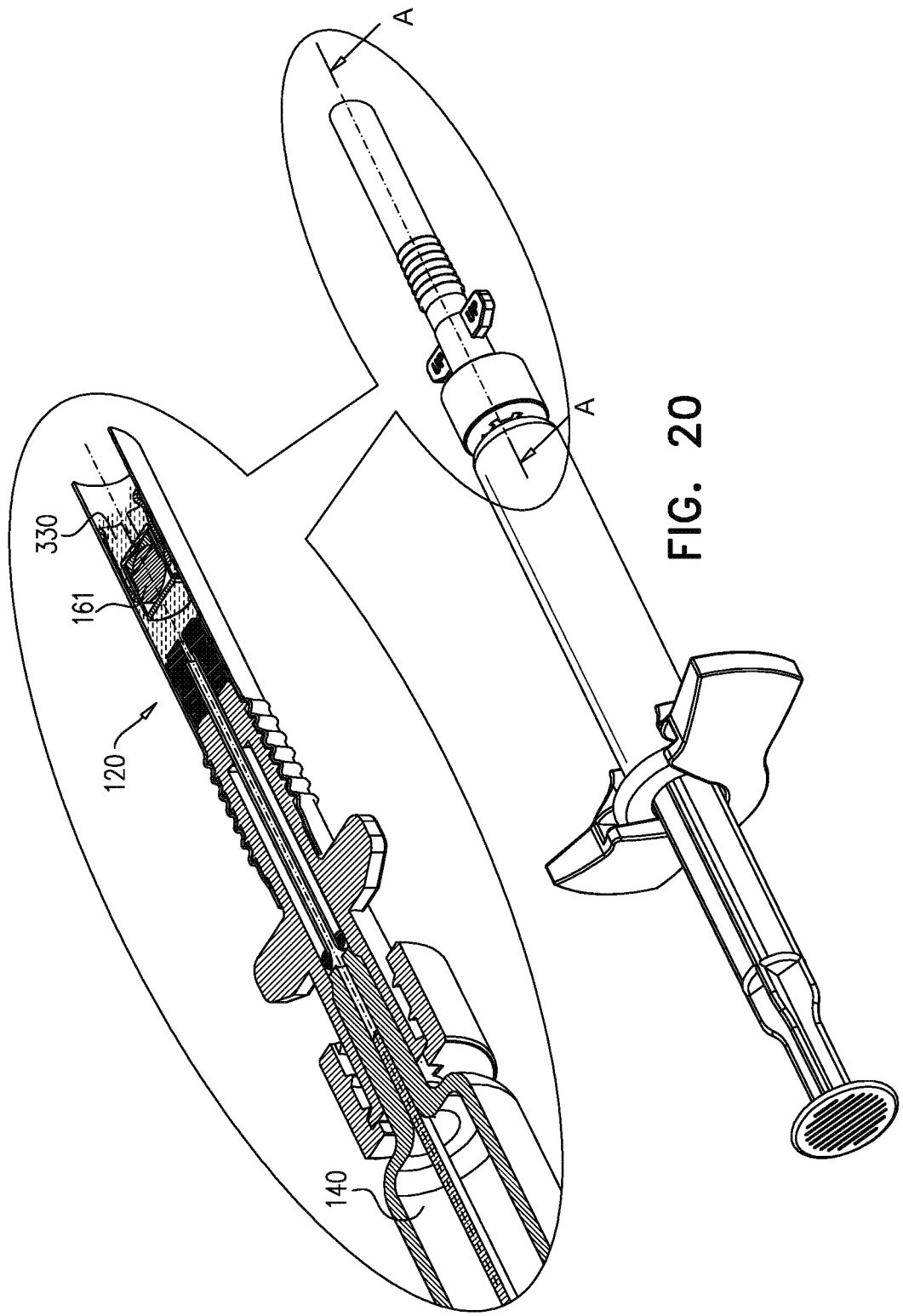
FIG. 20 is a simplified pictorial and enlarged partial pictorial sectional illustration, the sectional illustration taken along lines A-A, of part of the of the IOL implantation insertion assembly in a fifth operative orientation, ready for implantation of an intraocular lens.

Reference is now made to FIGS. 19A and 19B, which are simplified respective pictorial and planar sectional illustrations of the implantation assembly of FIG. 2 in a fourth operative orientation, following removal of safety catch 155 therefrom, and to FIG. 20, which is a simplified pictorial and enlarged partial pictorial sectional illustration, the sectional illustration taken along lines A-A, of part of the of the IOL implantation insertion assembly 120 in a fifth, operative orientation ready for implantation of an intraocular lens.

As seen in FIGS. 19A and 19B, following positioning of the IOL 161 within flexible sleeve 178, safety catch 155 is manually removed by a user to release implantation syringe 140, with IOL implantation insertion assembly 120 attached thereto, from main housing element 154. As seen in FIG. 20, IOL 161 and haptics 330 are located within IOL implantation insertion assembly 120 in a ready for implantation orientation.

It will be appreciated by persons skilled in the art that the present invention is not limited by what has been particularly shown and described hereinabove, rather the scope of the present invention includes both combinations and subcombinations of various features described hereinabove and modifications thereof which would occur to persons reading the foregoing description and which are not in the prior art.

The invention claimed is:

1. An apparatus for use in implanting intraocular lenses, the apparatus comprising:
   - an axial elongate hollow conduit having first and second ends and defining an intraocular lens injection pathway extending along a longitudinal axis, said axial elongate hollow conduit being formed at said first end with a syringe connector defining a removable syringe mounting location and being formed at said second end with an angled edge; and
   - a pusher element located within said axial elongate hollow conduit between said syringe connector and said second end,
   - at least one of said axial elongate hollow conduit and said pusher element including a fluid pathway for enabling viscoelastic material to pass through said syringe connector and said pusher element to a location between said pusher element and said second end of said axial elongate hollow conduit.

2. An apparatus for use in implanting intraocular lenses according to claim 1 and also comprising a dual purpose elongate hollow tube, fixed to said pusher element, said dual purpose elongate hollow tube having a fluid entry end adjacent said syringe connector and a fluid outlet end, said dual purpose elongate hollow tube defining a hollow pusher rod and being displaceable along said longitudinal axis within and relative to said axial elongate hollow conduit towards said second end, thereby displacing said pusher element along said axis towards said second end.

3. An apparatus for use in implanting intraocular lenses according to claim 2 and wherein said axial elongate hollow conduit includes a first relatively rigid housing portion, which defines said syringe connector, and a relatively flexible sleeve portion, which is mounted onto said relatively rigid housing portion.

4. An apparatus for use in implanting intraocular lenses according to claim 2 and wherein said hollow pusher rod is slidably and sealingly disposed within said axial elongate hollow conduit.

5. An apparatus for use in implanting intraocular lenses according to claim 4 and wherein said hollow pusher rod is slidably and sealingly disposed within said axial elongate hollow conduit by engagement with an O-ring.

6. An apparatus for use in implanting intraocular lenses according to claim 5 and wherein said hollow pusher rod is formed with a tapered opening, which communicates with a throughgoing cylindrical bore extending axially therethrough.

7. An apparatus for use in implanting intraocular lenses according to claim 6 and wherein said throughgoing cylindrical bore communicates with a conduit extending through said pusher element, thereby to define part of said mutually communicating conduits for enabling viscoelastic material to pass through said syringe connector and said pusher element to a location between said pusher element and said second end of said axial elongate hollow conduit.

8. An apparatus for use in implanting intraocular lenses according to claim 1 and wherein said axial elongate hollow conduit includes a first relatively rigid housing portion, which defines said syringe connector, and a relatively flexible sleeve portion, which is mounted onto said relatively rigid housing portion.

* * * * *